United States Patent [19]

McAnalley et al.

[11] Patent Number: 5,409,703

[45] Date of Patent: Apr. 25, 1995

[54] DRIED HYDROGEL FROM HYDROPHILIC-HYGROSCOPIC POLYMER

[75] Inventors: Bill H. McAnalley, Grand Prairie; Stephen Boyd, Tyler; Robert H. Carpenter, Bastrop; John E. Hall, Grand Prairie; Judith St. John, Irving, all of Tex.

[73] Assignee: Carrington Laboratories, Inc., Irving, Tex.

[21] Appl. No.: 82,028

[22] Filed: Jun. 24, 1993

[51] Int. Cl.$^6$ .................. A61K 9/70; A61L 15/26; A61L 15/60

[52] U.S. Cl. .................. 424/435; 424/423; 424/443; 424/78.06; 424/78.08; 424/145.1; 424/93.6; 536/128

[58] Field of Search ............... 424/423, 484, 435, 443, 424/78.06, 78.08, 195.1, 93 T; 536/128

[56] References Cited

U.S. PATENT DOCUMENTS

| | | | |
|---|---|---|---|
| 4,002,173 | 1/1977 | Manning et al. | 424/423 |
| 4,772,419 | 9/1988 | Malson et al. | 424/423 |
| 4,851,224 | 7/1989 | McAnalley | 514/847 |
| 5,079,018 | 1/1992 | Eranero et al. | 514/777 |
| 5,118,673 | 6/1992 | Carpenter et al. | 514/933 |

OTHER PUBLICATIONS

Physician's Desk Reference (1993) on Gelfoam ®.
Gelfoam ® (Upjohn): Suppl 4.
Gelfoam ® Products (Upjohn): SS&E Data, approved Jul. 8, 1983.
Gelfoam ® Gelatin Sponge (Upjohn): MOR, PH, TX, CH, Micro, P/I.
Thrombin vs Gelfoam ®—Compatibility DTA & Trans Jan. 6–Jul. 1979 Mtg.

*Primary Examiner*—Thurman K. Page
*Assistant Examiner*—Peter F. Kulkosky
*Attorney, Agent, or Firm*—Konneker Bush Hitt & Chwang

[57] ABSTRACT

A therapeutic medical device is described that is comprised of a dried hydrogel of a hydrophilic-hygroscopic polymer, such as an unmodified or modified polymeric carbohydrate, in the form of a solid foam. The dried hydrogel is prepared by preferably freeze-drying a hydrogel of this polymer in a liquid medium, such as water. The dried hydrogel can be sterilized by radiation or other means so that the sterilized product has a relatively indefinite shelf-life without refrigeration. The resultant dried hydrogel can be transformed into a hydrogel upon absorption of addition liquid medium. The described therapeutic device can serve as a dressing for a wound or lesion, drug delivery system, a hemostatic agent and a biologic response modifier. The described therapeutic device enhances the wound healing rate.

68 Claims, 6 Drawing Sheets

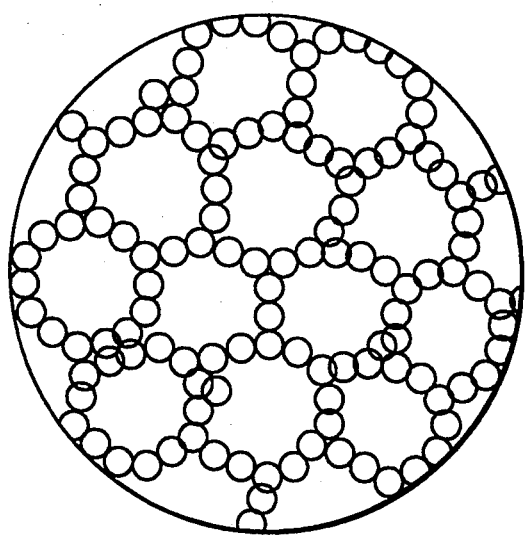
FIG. 1
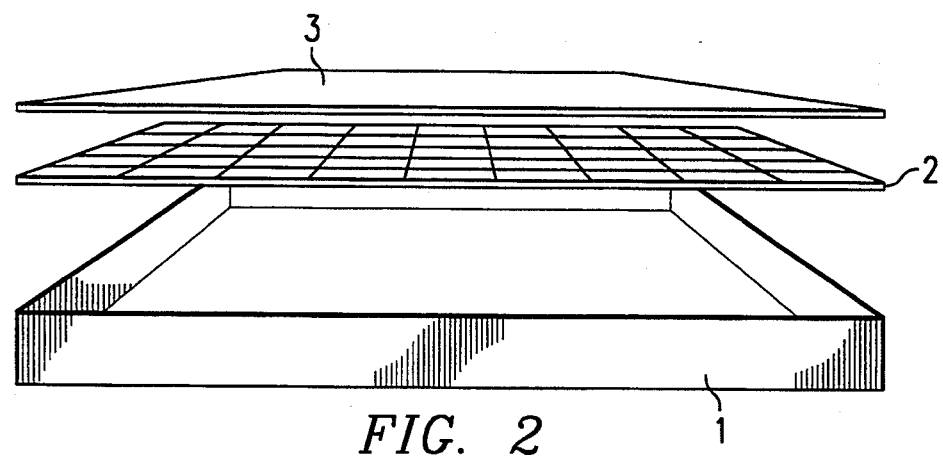
FIG. 2
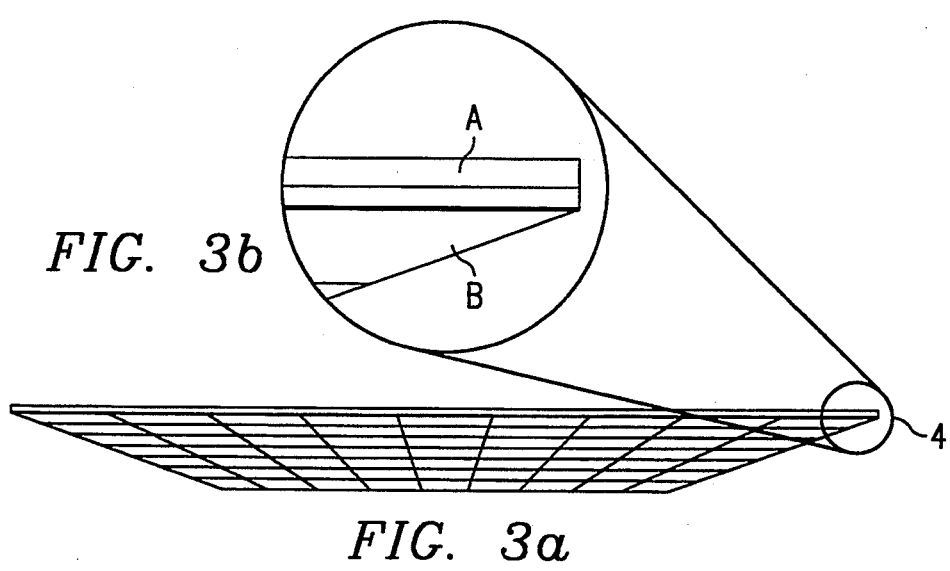
FIG. 3b
FIG. 3a

DRIED HYDROGEL FROM HYDROPHILIC-HYGROSCOPIC POLYMER

BACKGROUND

The present invention relates to a therapeutic medical device, as classified by the FDA, in the form of a solid foam, comprised of a dried hydrogel of hydrophilic-hygroscopic polymer, more particularly, freeze-dried hydrogel of a polymeric carbohydrate, such as acemannan, to be used as a wound/lesion dressing, a drug delivery system, a hemostatic agent or a biological response modifier.

I. WOUND MANAGEMENT

Wound healing is a complex series of biochemical and cellular events which result in the contracting, closing and healing of a wound, a traumatic insult to the integrity of a tissue. Wound management must protect the wound from additional trauma and/or environmental factors that would delay the healing process.

Wound management usually consists of a combined systemic and local approach, including the use of antibiotics and the application of a suitable dressing. The principal function of a wound dressing is to provide an optimum healing environment. For example, a wound must be isolated from the external environment before healing can begin. A wound dressing covers the wound mimicking the natural barrier function of the epithelium. To provide an optimum healing environment, a wound dressing should control bleeding, protect the wound from the external environment, prevent further contamination or infection and maintain a moist microenvironment next to the wound surface.

Contamination of a wound may result from contact with an infected object or the ingress of dirt, dust, or microorganism, either at the time of injury or later from the patient's own skin or gastrointestinal tract. For example, it has been found that, unless effective measures are taken to prevent infection, virtually all burns become colonized by bacteria within 12 to 24 hours. In general, infection impedes wound healing by further damaging tissue and promoting inflammation. Subsequent further wound repair is delayed by the progression of inflammation consisting of vascular leakage, the release and activation of lyric enzymes, free radical generation, oxygen consumption, and the sensitization of tissue nerve endings. Thus any measure that limits inflammation should promote wound healing provided that it does not compromise the tissue's ability to resist infection and essential macrophage function.

Up to and including the late 1950's, it was generally accepted that, in order to prevent bacterial infection, a wound should be kept as dry as possible. However, a variety of studies have questioned this philosophy and found that wounds that were kept moist actually healed more rapidly than those that were left exposed to the air or covered with traditional dried dressings. In a review of the properties of occlusive dressings, W. H. Eaglestein, "The Effect of Occlusive Dressings on Collagen Synthesis and Re-epithelialization in Superficial Wounds," *An Environment for Healing: The Role of Occlusion*, Ryan, T. J. (ed.) International Congress and Symposium Series No. 88, London, Royal Society of Medicine, pp. 31-38 (1985) concluded that occlusive dressings that keep wounds moist could increase the rate of epidermal resurfacing by some 40%.

II. AVAILABLE PRODUCTS

As a result of our greater understanding of the wound healing process, many new wound management products have been developed. Each of these products has its benefits and its deficits. In the case of large and/or irregular wounds, the available solid coverings such as gels, plastic, and gelatinous sheets generally do not maintain the close contact required for healing, especially for a wound with an irregular surface. Liquid gels cover the wound surface but are difficult to position and keep in place. In addition, they tend to become less stable at body temperature and flow out of the wound.

A. Absorbent Dressings

Semipermeable and impermeable wound dressings preserve the moisture in a wound but do not actively absorb excess moisture from the wound. The accumulation of wound fluid to the point of flooding can have severe consequences, including maceration and bacterial overgrowth. Dressings that are used to absorb exudate are frequently manufactured from cotton or viscous fibers enclosed in a sleeve of gauze. Such dressings are highly absorbent, but exhibit a tendency to adhere to the surface of the wound as fluid production diminishes. Furthermore, absorbent wound dressings generally do not provide adequate protection for the wound from the outside environment.

B. Nonadherent Dressings

Nonadherent dressings are designed not to stick to the wound. Gauze is often impregnated with paraffin or petroleum jelly to provide a nonadherent dressing. However, the impregnate can wear off, necessitating a dressing change and traumatizing new tissue growth.

In addition to the impregnated gauze type, nonadherent dressings may consist of an absorbent pad faced by a preformed nonadherent film layer.

C. Hydrogel Dressings

Hydrogels are complex lattices in which the dispersion medium is trapped rather like water in a molecular sponge. Available hydrogels are typically insoluble polymers with hydrophilic sites, which interact with aqueous solutions, absorbing and retaining significant volumes of fluid.

Hydrogel dressings are non-adherent and have a higher water content. Hydrogels have been reported to increase epidermal healing. Hydrogels progressively decrease their viscosity as they absorb fluid. In liquefying, hydrogels conform to the shape of the wound and their removal is untraumatic. However, currently available hydrogels are not biodegradable and do not consistently enhance the complete healing process.

D. Absorbable Materials

Absorbable materials are degraded in vivo and do not require removal. Particularly useful internally as hemostats, these materials include collagen, gelatin, and oxidized cellulose.

Gelfoam ®, an absorbable gelatin sponge, has been available and used in various surgical procedures as a topical hemostatic agent since the mid 1940's. Gelfoam ®, a brand of absorbable gelatin sterile sponge manufactured by Upjohn, is a medical device intended for application to bleeding surfaces as a hemostatic. It is a water insoluble, off-white, non-elastic, porous, pliable product prepared from purified porcine skin collagen. It can absorb and hold within its interstices, many times its weight of blood and other fluids. When not used in excessive amounts, Gelfoam ® is absorbed completely, with little tissue reaction. This absorption is dependent on several factors, including the amount used, degree of saturation with blood or other fluids, and the site of use.

When placed on soft tissues, Gelfoam ® is usually absorbed completely in four to six weeks, without inducing excessive scar tissue.

The *Physician's Desk Reference* (1993 edition) suggests that one use only the minimum amount of Gelfoam ® sterile sponge needed to achieve hemostasis, holding it at the site of injury until bleeding stops. Once hemostasis is reached, one should carefully remove any excess Gelfoam ® as it may interfere with the healing of skin edges. Furthermore, Gelfoam ® must not be placed in intravascular compartments because of the risk of embolization.

In addition, Gelfoam ® is not recommended for use in the presence of an infection. If signs of infection or abscess develop where Gelfoam ® has been positioned, reoperation may be necessary in order to remove the infected material and allow drainage.

Another precaution is that Gelfoam ® should not be used in conjunction with autologous blood salvage circuits as it has been demonstrated that fragments of microfibular collagen pass through the 40 micron transfusion filters of blood scavenging systems.

E. Polysaccharide Dressings

One of the oldest and most enduring materials used in wound management is honey, a complex mixture consisting principally of glucose and fructose. Honey has a low pH, about 3.7, which creates an unfavorable environment for bacterial growth. However, honey has a high osmotic pressure and will effectively draw water out of the surrounding tissue and may dehydrate regenerating epithelial cells.

In recent years, there has also been an increasing interest in the use of sugar, sucrose, as a wound dressing. However, commercial sugar supplies are not always sterile and may contain calcium phosphate, sodium aluminum silicate, or other salts. Although the topical use of sugar appears to be relatively free of adverse effects, sugar has not been shown to be effective as the sole treatment of wounds in controlled clinical tests and may tend to dehydrate epithelial cells, macrophages and fibroblasts.

Available polysaccharide dressings such as Debrisan ™, a linear polymer of glucose manufactured by Pharmacia, come formed into beads or granules that are poured into a wound and covered with a simple dressing pad or a semipermeable plastic film. The mobile nature of the beads can make Debrisan ™ difficult to use in a shallow wound although the beads do provide a highly absorbent material that is biodegradable.

III. PHARMACOLOGICAL PROPERTIES OF POLYSACCHARIDES

There are many examples in the literature indicating that polysaccharides can exhibit pharmacological and physiological activities without help from other components. Gialdroni-Grassi, *International Archives of Allergy and Applied Immunology*, 76 (Suppl. 1):119–127 (1985); Ohno et al., *Chemical and Pharmaceutical Bulletin*, 33(6):2564–2568 (1985); Leibovici et al., *Chemico-Biological Interactions*, 60:191–200 (1986); Ukai et al., *Chemical and Pharmaceutical Bulletin*, 31:741–744 (1983); Leibovici et al., *Anticancer Research*, 5:553–558 (1985). One such example relates to development of atherosclerosis. Hyperlipidemia in the general population and especially in familial hypercholesterolemia is associated with coronary heart disease and death. In countries where dietary fiber intake is high, atherosclerosis appears to be uncommon. Trowell et al., Editors, *Refined Carbohydrate Foods and Disease*, London, Academic Press, 207 (1975). Pectin and guar are reported to lower cholesterol in normal and hyperlipidemic patients. Kay et al., *American Journal of Clinical Nutrition*, 30:171–175 (1977). Locust bean gum, a polysaccharide composed of mannose and galactose, decreased the plasma lipoprotein cholesterol concentrations in both normal and familial hypercholesterolemic subjects. Zavoral et al., *American Journal of Clinical Nutrition*, 38:285–294 (1983). Addition of guar gum to carbohydrate meals decreased the postprandial rise of glucose in both normal and diabetic subjects. Jenkins et al., *Lancet*, 2:779–780 (1977). Kuhl, et al., in *Diabetes Care*, 6(2):152–154 (1983) demonstrated that guar gum exhibited glycemic control of pregnant insulin-dependent diabetic patients.

The antitumor activity of polysaccharides has been widely reported. Polysaccharides prepared from *Lentinus cyathiformis* are known to increase host defense against tumors. Rethy et al., *Annales Immunologia Hungaricae*, 21:285–290 (1981). There are several reports that polysaccharides from mushroom, yeast or bacterial extracts can elicit a high degree of host defense activity against vital and tumor infestations. Chihara, *Nature*, 222:687 (1969); Shwartzman et al., *Proceedings of the Society for Experimental Biology and Medicine*, 29:737–741 (1932); Suzuki et al., *Journal of Pharmacobio-Dynamics*, 7(7):492–500 (1984), also reported antitumor activity of a polysaccharide fraction (GF-1) extracted from cultured fruiting bodies of a fungus. *Grifola frondosa*. This fraction showed equivalent, high levels of inhibiting activity when administered intraperitoneally (IP), intravenously (IV) or intratumorally (IT). However, oral administration (PO) was not effective. The GF-1 fraction also exhibited antitumor action against the solid form of Meth A fibrosarcoma and MM 46 carcinoma in mice. Lentinan, which is a 6-branched $\beta$-1-3-linked glucan similar to GF-1, was ineffective against Meth A fibrosarcoma. Chihara, "The antitumor polysaccharide Lentinan: an overview;" *Manipulation of Host Defense Mechanisms;* Ed. by Aoki et al, *Excerpta Medica*, North Holland, 1–16 (1981); Sasaki et al. , *Carbohydrate Research*, 47(1):99–104 (1976).

Synthesized branched polysaccharides were also reported to demonstrate anti-tumor activity. Matsuzaki et al., *Makromol Chem.*, 186(3):449–456 (1985). Matsuzaki et al., [*Makromol. Chem.*, 187(2):325–331 (1986)] synthesized branched polysaccharides, which showed significant activities, both $\beta$-(1-4)-D-mannopyranose and $\beta$-(1-4)-linked glucomannan. A partially acetylated linear $\beta$-(1-3)-D-mannan extracted from fruit bodies of *Dictyophoria indusiata* Fisch, also exhibited antitumor activity. Hara, *Carbohydrate Research*, 143:111 (1982). It appears that antitumor action depends on the type of polymer main chain and its degree of polymerization, because $\beta$-(1-3)-glucan-type polymers show higher antitumor activity than $\beta$-(1-4)-glucan and hemicellulosic polymers. Matsuzaki et al., *Makromol. Chem.*, 187:325–331 (1986). A carboxymethylated derivative of $\beta$-(1-3)-glucan obtained from bacterial culture filtrate caused severe cell loss from established sarcoma 180 tumors within 2 hours after the injection of the derivative. Baba, *Journal of Immunopharmacology*, 8(6):569–572 (1986). The same author observed a compensatory increase in polymorphonuclear leukocytes due to injection of the substance. Incidentally, bestatin, a dipeptide known to possess immune-modulating and antitumor activity [Ishizuka, *Journal of Antibiotics*, 32:642–652 (1980)], influenced neither the tumor yield nor the polymorphonuclear leukocyte count. Baba et al., supra.

There are numerous reports on the antitumor effect of sulfated polysaccharides, including heparin [Jolles et al., *Ata Univ. Int. Cancer*, 16:682–685 (1960); Suemasu et al., *Gann*, 61(2):125–130 (1970)], sulfated laminaran and dextran [Jolles et al., *British Journal of Cancer*, 17:109–115 (1963)]. Yamamoto et al., in *Japanese Journal of Experimental Medicine*, 54:143–151 (1984), reported enhancement of antitumor activity of a fucoidan fraction by further sulfation. The sulfated product demonstrated activity against L-1210 leukemia. The authors postulated that the mechanism of the antitumor action might be due partly to inhibition of invasive growth of L-1210 cells, as a result of electrostatic repulsion between the tumor cell and mesothelial cells. Yamamoto et al., supra. Polysaccharides with sulfate groups are also reported to be human T cell mitogens and murine polyclonal B cell activators. Sugawara et al., *Microbiological Immunology*, 28(7):831–839 (1984). Generally, homopolysaccharides of high molecular weight with sulfate groups possess these properties. Dorries, *European Journal of Immunology*, 4:230–233 (1974); Sugawara et al., *Cell Immunology*, 74:162–171 (1982).

It has been reported that glucan extracted from the yeast *Saccharomyces cervisiae* is a modulator of cellular and humoral immunity. Wooles et al., *Science*, 142:1079–1080 (1963). The extracted glucan also stimulated proliferation of murine pluripotent hematopoietic stem cells, granulocyte macrophage colony-forming cells and cells forming myeloid and erythroid colonies. Pospisil et al., *Experientia*, 38:1232–1234 (1982); Burgaleta, *Cancer Research*, 37:1739–1742 (1977). Maisin et al., [*Radiation Research*, 105:276–281 (1986)] also reported that IV administration of a polysaccharide induced protection of murine hematopoietic stem cells against x-ray exposure, thereby decreasing the mortality of the mice so exposed.

Lackovic et al., [*Proceedings of the Society for Experimental Biology and Medicine*, 134:874–879 (1970)], took yeast cell wall and extracted all constituent matter leaving only "mannans" that he found to be responsible for the induction of an interferon production by peritoneal leukocytes. The "purified mannans" alleged to be responsible for this physiologic response had a molecular weight of 5,500–20,000 Daltons. He theorized that mannans stimulated mouse peritoneal macrophages to produce γ-interferon. He also stated that the mannans he isolated showed no toxicity and "they are poor antigens." There was no mention by Lackovic et al. of the use of these "purified mannans" for antiviral activity or for IL-1 stimulation. We submit that Lackovic et al.'s "purified mannans" comprised an assortment of unknown and unidentified substituted and unsubstituted mannans.

Seljelid et al., [*Experimental Cell Research*, 131(1):121–129 (1981)] have observed that insoluble or gel-forming glycans activated macrophages in vitro, whereas the corresponding soluble glycans did not. They postulated that the orientation in which the glycan was presented to the mononuclear phagocyte was decisive for activation. Bogwald, [*Scandinavian Journal of Immunology*, 20:355–360 (1984)] immobilized glycans that had a stimulatory effect on the macrophages in vitro. This led the authors to believe that the spatial arrangements of the glycan was decisive for the effect on the macrophages in vitro. A purified polysaccharide isolated from *Candida albicans* induced an antibody response by human peripheral blood lymphocytes in vitro. Wirz et al., *Clinical Immunology and Immunmopathology*, 33:199–209 (1984). Yet there were significant differences between the antiCandida antibodies in sera of normal and Candida-infected individuals. Wirz et al., supra.

As discussed above, the biological activities of polysaccharide materials recovered from plants, yeast and bacteria have demonstrated direct biological activities by eliciting an increase in host defense systems. This reaction is primarily manifested by increased host surveillance for other antigenic substances. Polysaccharides serve as adjuvants (DEAE, Dextran, etc.) and immunomodulators. They also can function as unique T-cell-independent antigens. Both cellular and humoral immunity may be affected, and increased phagocytosis of infectious organisms and tumor cells has been observed, as has enhanced production of immunoglobulins.

The structure of these immunologically active polysaccharides and the types of structural variations appear to be the factors that control their potency and toxicity. Their mode(s) of action remain poorly understood; however, recent evidence indicates that several polysaccharides induce lymphocytes and macrophages to produce a wide range of immunologically active substances. For example, 2-keto-3-deoxy-D-manno-octulosonic acid (KDO) appears to be the chemical portion of lipopolysaccharide (LPS) that provides the minimum signal for macrophage host defense activation [Lebbar et al., *Eur. J. Immunol*, 16(1):87–91 (1986)].

The antiviral activity of polysaccharides and polysaccharides linked to peptides has been observed. Suzuki et al., *Journal of Antibiotics*, 32:1336–1345 (1979). Suzuki et al, supra, reported an antiviral action of peptidomannan (KS-2) extracted from mycelial culture of *Lentinus edodes*. Both oral and intraperitoneal administration increased the peak serum interferon titer, which protected mice against vital infections. This was different from dextran phosphate (DP-40) [Suzuki et al., *Proceedings of the Society for Experimental Biology and Medicine*, 149(4):1069–1075 (1975)] and 9-methylstreptimidone (9-MS) [Saito et al., *Antimier, Agent & Chemotherapy*, 10(1):14–19 (1976)], which induced higher titers of interferon in mice only if administered IV or IP.

Other researchers have also reported effects of complex polysaccharides [Saeki et al., *Japanese Journal of Pharmacology*, 24(1):109–118 (1974)], glycoproteins [Arita et al., *Journal of Biochemistry*, 76(4):861–869 (1974)] and sulfated polysaccharides [Rocha et al., *Biochemical Pharmacology*, 18:1285–1295 (1969)].

Ukai et al., [*Journal of Pharmacobio-Dynamics*, 6(12):983–990 (1983)] noted activity of polysaccharides extracted from the fruiting bodies of several fungi. The polysaccharides demonstrated a significant inhibitory effect on carrageenan-induced edema in rats. One of the polymers, O-acetylated-D-mannan (T-2-HN), in addition, demonstrated a more marked inhibitory effect than phenylbutazone on scald hyperalgesia. Ukai et al., supra. The assertion that the polysaccharide is free from protein and lipids strongly suggests that the effect is due to the acetylated mannan only.

Mannans, including glucomannans and galactomannans, have long been used by man. For example, galactomannans, in the form of plant gums, are widely employed as binders for control of food texture. In addition, some mannans have exhibited significant therapeutic properties [Davis and Lewis, eds. Jeanes, A., Hodge, J., In: American Chemical Society Symposium, Series 15, Washington, D.C., American Chemical Society, 1975]. Practitioners of Japanese folk medicine have long believed that extracts of certain fungi have anticancer activity. On investigation, many of these extracts have been found to contain complex carbohydrates with immune-stimulating activity. These carbohydrates are usually polymers of mannose (mannans), glucose (glucans), xylose (hemicellulose), fructose (levans) and mixtures of these. Individual sugars may be bonded in different ways as chains may be branched or unbranched. Glucans have been the most widely studied of these immunostimulatory carbohydrates. It has become increasingly clear that even though they have no toxicity mannans are as effective, if not more effective, than glucans.

IV. PROPERTIES OF ACEMANNAN

A. Purified from Aloe vera

Aloe is a member of the lily family, Harding. *Aloes of the World: A Checklist, Index and Code, Excelsa* 9:57–94 (1979). *Aloe barbadensis* Miller is generally recognized as the "true aloe" because of its wide use and, reportedly, most effective healing power. Although in Japan, *Aloe arborescens* Miller traditionally has been used as a folk remedy for various ailments ranging from gastrointestinal disorders to athlete's foot. Aloe vera is a perennial plant with turgid green leaves joined at the stem in a rosette pattern. The leaves of a mature plant may be more than 25 inches long with sawlike spikes along their margins.

Aloe vera contains two major liquid sources, a yellow latex (exudate) and the clear gel (mucilage). The dried exudate of *Aloe barbadensis* Miller leaves is referred to as aloe. The commercial name is Curacao aloe. It is composed mainly of aloin, aloe-emodin and phenols. Bruce, *South African Medical Journal*, 41:984 (1967); Morrow et al., *Archives of Dermatology*, 116:1064–1065 (1980); Mapp et al., *Planta Medica*, 18:361–365 (1970); Rauwald, *Archives Pharmazie*, 315:477–478 (1982). A number of phenolics, including anthroquinones and their glycosides, are known to be pharmaceutically active. Bruce, *Excelsa*, 5:57–68 (1975); Suga et al., *Cosmetics and Toiletries*, 98:105–108 (1983).

The mucilaginous jelly from the parenchymal cells of the plant is referred to as Aloe vera gel. There are generally no anthroquinones to decompose and cause discoloration of the gel unless the gel is contaminated by an improper processing technique. Aloe vera gel is about 98.5% water by weight. More than 60% of the total solid is made up of polysaccharides of carbohydrate origin. Organic acids and inorganic compounds, especially calcium oxalate, account for the remainder of the solid residue.

Whole leaves, exudates and fresh gels of Aloe plants have been used for a variety of human afflictions. Evidence of their use as a medicinal remedy can be traced to the Egyptians of 400 BC. Aloe vera was also used to embalm the dead, as well as to protect the embalmers from the death-causing agent. Other early civilizations used Aloe vera for skin care, to relieve insect stings and bites, to treat scratches and ulcerated skin, to promote wound healing, to prevent hair loss and as a purgative. Aloe vera was used in the traditional medicine of many cultures as an anthelmintic, cathartic and stomachic and was used inter alia for leprosy, burns and allergic conditions. Cole et al., *Archives of Dermatology and Syphilology*, 47:250 (1943); Chopra et al., *Glossary of Indian Medicinal Plants*, Council of Scientific and Industrial Research, New Delhi (1956); Ship, *Journal of the American Medical Association*, 238(16):1770–1772 (1977); Morton, *Atlas of Medicinal Plants of Middle American Bahmas to Yucatan*, Charles C. Thomas Publisher, 78–80 (1981); Diez-Martinez, La Zabila, *Communicado NO. 46 Sobre Recursos Bioticos Potenciales del Pais*, INIREB, Mexico (1981); Dastur, *Medicinal Plants of India and Pakistan*, D. B. Taraporevala Sons & Co., Private Ltd., Bombay 16–17 (1962).

Depending on the way the leaves are processed, mucilage and sugars are the major components of the dehydrated gel. The sugars found are galactose, glucose, mannose, rhamnose, xylose and uronic acids. Although reports conflict, the mucilage is mainly composed of mannan or glucomannan. Eberendu et al., *The Chemical Characterization of Carrisyn ®* (in preparation); Mandal et al., *Carbohydrate Research*, 86:247–257 (1980b); Roboz et al., *Journal of the American Chemical Society*, 70:3248–3249 (1948); Gowda et al., *Carbohydrate Research*, 72:201–205 (1979); Segal et al., *Lloydia*, 31:423 (1968).

For a long time, the controversy over the identity of the active substance(s) in Aloe vera was not settled. It is therefore important to clearly distinguish between the components present in the gel and those found in the exudates. A majority of the gel is a mucilage of mainly polysaccharide nature with minor amounts of various other compounds. It has been observed that in some of the activities there may be some synergistic action between the polysaccharide base and other components. Leung, *Excelsa*, 8:65–68 (1978); Henry, *Cosmetics and Toiletries*, 94:42–43, 46, 48, 50 (1979). For example, several workers report that the effective components for wound healing may be tannic acid [Freytag, *Pharmazie*, 9:705 (1954)] and a kind of polysaccharide. Wound-healing compositions from Aloe arborescens extracts. Kameyama, Japanese Patent #7856995, (1979). Mackee, supra, noted that the gel, not the rind or the exudate, was responsible for the beneficial effects in the treatment of radiation burns, and he stressed the importance of using fresh leaves for effective treatment. Polysaccharides degrade with time, and certain molecular weight sizes may be necessary to elicit a specified pharmacological response. Goto, et al., *Gann*, 63:371–374 (1972).

Literature which reports that polysaccharides possess pharmacological and physiological activities continues to flood the pages of well-respected scientific journals. It is therefore logical that the mucilaginous gel of the Aloe vera plant, which is essentially a polysaccharide, holds the secret to Aloe vera's medicinal properties. The controversy over whether the polysaccharide is a glucomannan, mannan, pectin, or of some other composition, is resolved by a series of chemical purification steps. Yagi et al., [*Planta Medica*, 31(1):17–20 (1977)], using a slightly modified extraction method, isolated acetylated mannan (aloe mannan) from *Aloe arborescens* Miller var natalensis. Ovodova [*Khim, Prior. Soedin*, 11(1):325–331 (1975)], however, earlier isolated pectin as the main component of the same aloe species.

B. Chemical Properties of Acemannan

Carrisyn ® is the brand name given by the assignee of the instant invention to the purified ethyl alcohol extract of the inner gel of the leaves of *Aloe barbadensis* Miller. The active component of Carrisyn ® has been designated "acemannan" by the United States Adopted Name Council. Not less than 73% of Carrisyn ® extract is acemannan: Carrisyn ® extract comprises generally about 73% to 90% acemannan. Carrisyn ® extract is generally produced by removing the outer sheath of the leaf, then removing and processing the inner filet or mucilage as follows: pH adjustment, ethanol extraction, freeze drying and grinding. See U.S. application Ser. No. 144,872 filed January 1988 (now U.S. Pat. No. 4,851,224), a continuation-in-part of U.S. application Ser. No. 869,261 (now U.S. Pat. No. 4,735,935), the disclosures of all of which are incorporated herein by reference. Processing in this manner predicts that essentially no covalent bonds are altered and therefore no toxic compounds or byproducts are created. These manufacturing steps were developed to overcome the inability of traditional aloe product producers to standardize and stabilize the polysaccharides.

Acemannan is a fluffy, white, amorphous slightly hygroscopic powder, which is poorly soluble in water and dimethyl sulfoxide and insoluble in most other organic solvents. This powder consists of linear $\beta(1\text{-}4)$-D-mannosyl units. The polysaccharide is a long chain polymer interspersed randomly with acetyl groups linked to the polymer through an oxygen atom. The generic name for the polymer is acemannan. The degree of acetylation is approximately 0.91 acetyl groups per monomer as determined by the alkaline hydroxamate method. See Hestrin, *Journal of Biological Chemistry*, 180:240–261 (1949). Neutral sugars linkage analysis indicates that attached to the chain, probably through an $\alpha(1\text{-}6)$ linkage, is a D-galactopyranose in the ratio of approximately one for every 70 sugars. The 20:1 ratio of mannose to galactose indicates that galactose units are also linked together, primarily by a $\beta(1\text{-}4)$ glycosidic bond. The chemical structure of acemannan may be represented as follows:

A study was performed using human peripheral blood monocyte cell cultures and $^{14}$C-labeled acemannan to track the incorporation or absorption of acemannan into a biological system. In this study, detectable amounts of $^{14}$C-labeled acemannan were absorbed or ingested by human peripheral monocyte/macrophage cells. Peak incorporation occurred at 48 hours. At a concentration of 5 mg/ml, the $^{14}$C-labeled acemannan was not cytotoxic to the monocyte/macrophage cells, and the weight/volume (w/v) digested cell mass was 760 times greater than the w/v of the digested acemannan solution. These results suggest that the macrophage is capable of maintaining intracellular concentration of acemannan at very high levels that are not cytotoxic.

A pyrogen assay was per,formed in rabbits in accordance with the pyrogen test protocol outlined in the U.S.P. XXI. Biological Test [151] using a 1 mg/ml injectable solution of acemannan. More frequent temperature measurements were taken than specified in the U.S.P. because of the unknown systemic effects of injected acemannan. Temperature changes in test animals did not exceed minimum changes allowed by the U.S.P. protocol; therefore, the solution met the U.S.P. requirements for absence of pyrogens. Injected acemannan elicited a maximum body temperature increase of 0.3° C. in one rabbit. This temperature rise occurred 90 minutes after injection. Acemannan is an inducer of IL-1 secretion by macrophages and monocytes in vitro. Since IL-1 is a potent pyrogen, this might explain the minimal, delayed temperature rise in this rabbit.

Twenty-four human subjects enrolled in and completed the study of the safety and tolerance of orally-administered acemannan. Clinical laboratory results showed that shifts out of the normal range occurred in General Structure of Ultrapure Acemannan

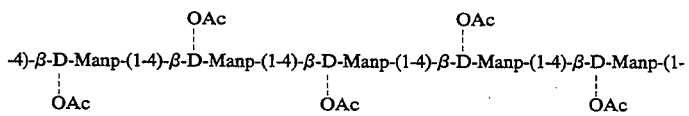

p = Pyranose

C. Toxicology

The toxicological effects of acemannan have been studied in both in vivo and in vitro systems. Acemannan is not mutagenic or blastogenic in in vitro test systems. In vitro, the compound showed no detectable toxicity for H-9, MT-2 and CEM-SS lymphoid cells. In vivo toxicology studies on acemannan include a 91-day subchronic oral toxicity study in dogs, a 180-day chronic oral toxicity study in rats and a 180-day clinical trials in humans. In these studies, no toxic effects were noted in dogs receiving up to 825 mg/kg of acemannan per day for 91 days. No clinical, gross pathologic or toxic effects were noted in rats receiving up to 38.475 ppm acemannan in their feed for 180 days. No adverse clinical or toxic effects were noted in human patients receiving 800 mg per day of acemannan for 180 days in clinical trials.

In pilot studies, administration of acemannan to dogs caused an absolute monocytosis in blood samples taken for complete white blood cell counts and morphology differential. Within 2 hours after oral administration of high doses of acemannan, large activated monocytes appeared in circulation. A similar effect has been observed in humans.

the following: $CO_2$ in seven subjects, cholesterol in three subjects, triglycerides in two subjects, phosphorous in one, hemoglobin in four, basophils in two, monocytes in three, eosinophils in three, lymphocytes in four, neutrophils in two, and one each in red and white blood cells. Small numbers of red and white blood cells were also found in the urine. None of these shifts was clinically relevant.

Immune profile results showed group differences between Day 1 to Day 7 values for the following: CD-16, CD4 (T-4), CD-8-Leu7, CD-4-CD-25, CD-8-CD-16, Leu7 and TQ-1. Mitogen responses were in the low range.

Vital signs did not appear to exceed normal ranges. There were no group differences in urine output. One subject in Group IV had diarrhea and loose stools during the study. One subject in Group I had loose stools during days 2 to 4 of the study. A total of 5 subjects reported a total of eight adverse events. All the events occurred in subjects receiving 1600 or 3200 mg oral acemannan daily for 6 days.

D. Pharmacological Properties of Acemannan

Aloe vera has enjoyed a long history of lay acceptance as possessing "curative" or "healing" qualities.

Over the last few years, numerous books and articles meeting scientific standards have been written on Aloe vera. Organizations such as the International Aloe Vera Science Council and recognized medical institutions, through publications and case histories of physicians, veterinarians and other scientists, have given credence to the "aloe phenomenon." Aloe vera has been featured extensively in the field of dermatology, especially for treating radiation-caused skin conditions. Mackee, *X-rays and Radium in the Treatment of Diseases of the Skin*, 3rd Ed., Lea and Febiger, Philadelphia, 319–320 (1938); Rovatti et al., *Industrial Medicine and Surgery*, 28:364–368 (1959); Zawahry et al., *Quotations From Medical Journals and Aloe Research*, Ed. Max B. Skousen, Aloe Vera Research Institute, Cypress, Calif., 18–23 (1977); Cera et al., *Journal of the American Animal Hospital Association*, 18:633–638 (1982). The body of scientific literature documenting medical applications in digestive problems, as a virucidal, bactericidal and fungicidal agent and in gynecological conditions is extensive and has been adequately reviewed by Grindley et al., [*Journal of Ethnopharmacology*, 16:117–151 (1986)].

A number of pharmacology studies have been conducted on Aloe vera gel in recent times. Results have included more rapid healing of radiation burns [Rowe, *J. Am Pharm. Assoc.*, 29:348–350 (1940)] and accelerated healing of wounds [Lushbaugh et al., *Cancer*, 6:690–698 (1953)]. Thermal burns treated with Aloe vera gel heal much faster than untreated burns [Ashley et al., *Plast. Reconstr. Surg.*, 20:383–396 (1957). Rovatto, supra. Rodriguez-Bigas et al., *J. Plast. Reconstr. Surg.*, 81:386–389 (1988)]. The gel is useful in treating leg ulcers [El Zawahry et al., *Int. J. Dermatol*, 12:68–73 (1973)] and in hastening post surgical healing (Payne, Thesis submitted to Faculty of Baylor University, Waco, Tex., MS Degree). Experimental evidence suggests that extracts of Aloe vera have anti-infectious properties [Solar, *Arch. Inst. Pasteur Madagascar*, 47:9–39 (1979)] and enhance phagocytosis [Stepanova, *Fiziol, Akt. Veshchestva*, 9:94–97 (1977)].

Acemannan has also been shown to be a potent stimulator of the immune system. Acemannan induces the production of Interleukin 1 (Il-1) and prostaglandin $E_2(PGE_2)$ in human peripheral blood adherent cells in culture. Acemannan has been shown to be effective as an adjuvant and immunoenhancer and can be effectively used to treat cancer, vital disease, and infections. See U.S. Pat. No. 5,106,616 and U.S. Pat. No. 5,118,673 and references cited therein, the disclosures of which are incorporated herein by reference. All of these patents and this patent application are also assigned to Cartington Laboratories, Inc.

Despite the known therapeutic properties of many polysaccharides, despite the availability of various gels for treating a wound or lesion, and despite the obtainability of certain "water-insoluble" foam devices, there is a need for a relatively dry and flexible foam-like therapeutic device that can promote the healing of a wound or lesion, that can act as a drug delivery system, that can act as a biological response modifier, and that can transform into a relatively clear hydrogel upon absorption of a fluid, either a therapeutic liquid/suspension or body fluid.

SUMMARY OF THE INVENTION

It is therefore an object of the present invention to produce a relatively dry and flexible solid foam-like therapeutic medical device that can function as a wound/lesion dressing and that can easily be cut or shaped to the contours of the wound or lesion.

It is another object of this invention to provide a therapeutic device for a wound/lesion dressing that has a relatively indefinite shelf-life without refrigeration.

It is yet another object of the present invention to make a therapeutic device for a wound/lesion dressing that can be easily sterilized by ultraviolet light, dry heat, gas or other radiation and does not require the incorporation of a preservative. Preservatives in a wound/lesion dressing may dehydrate the interface between the wound/lesion, sting the patient, and/or inhibit the cell proliferation and the optimal growth of new tissue.

It is still another object of the present invention to provide a therapeutic device that can function as a wound/lesion dressing that is transparent when wet and thus allows one to visually follow the healing process without removing the dressing.

It is yet another object of the present invention to provide a therapeutic device that can function as a wound/lesion covering that is, when wet, self-adherent and will remain in contact with the target site without the need of a potentially toxic adhesive.

It is still yet another object of the present invention to provide a therapeutic device that can function as a wound/lesion dressing that can be used in either an absorptive format or as a non-absorptive hydrogel to protect the underlying regenerating tissue. The present invention can be applied as a dried foam that will absorb excess fluid, which may contain harmful components as a result of infection or contamination, from a wound/lesion and be converted into a hydrogel. The present invention may also be applied as a hydrogel, prepared by presoaking the relatively dried foam in saline or other therapeutic liquid/suspension, to traumatized areas that do not require exudate removal.

It is a further object of the present invention to provide a therapeutic device that can function as a wound/lesion dressing that will accelerate the healing process.

It is a still further object of the present invention to provide a therapeutic device that can function as a wound/lesion dressing that will actively act as anti-infective agent to protect the wound/lesion from contamination.

It is yet a further object of the present invention to provide a therapeutic device that can function as a wound/lesion dressing that will serve as an active immune enhancer.

It is another object of the present invention to provide a therapeutic device that can function as a wound/lesion dressing that is biodegradable and does not have to be removed from the application site.

It is yet another object of the present invention to provide a therapeutic device that can serve as a drug delivery system for antibiotics, anesthetics, and other pharmaceutical agents.

It is still yet another object of the present invention to provide a therapeutic device that can deliver a high concentration of acemannan per unit weight at the trauma site.

In short, one general object of the present invention is to provide a therapeutic device that can function as a wound/lesion dressing that can ensure that the wound/lesion remains moist but not macerated with infection control, free of toxic substances, and undisturbed by dressing changes.

Broadly, one aspect of the present invention pertains to a therapeutic device comprising a dried hydrogel in the form of a solid foam prepared by removing, from a hydrogel, a liquid medium, such as water, in a dispersed phase from particles of a hydrophilic-hygroscopic polymer, in a dispersion phase; the dried hydrogel is capable of being transformed into the hydrogel upon absorption of additional liquid medium.

In one embodiment, the dried polymeric carbohydrate hydrogel in a solid foam form is comprised of from about 85 to about 95% (W/W) of a polymeric carbohydrate dispersed in from about 5 to about 15% (W/W) of water.

The foregoing has outlined rather broadly the features and technical advantages of the present invention in order that the detailed description of the invention that follows may be better understood. Additional features and advantages of the invention will be described hereinafter which form the subject of the claims of the invention.

BRIEF DESCRIPTION OF THE DRAWINGS

For a more complete understanding of the present invention, and the advantages thereof, reference is now made to the following descriptions taken in conjunction with the accompanying drawings, in which:

FIG. 1 shows a picture of a hydrogel.

FIG. 2 shows a schematic of a lyophilizer tray with a backing material and dispersion of polysaccharide.

FIG. 3a shows a cross-section of a freeze-dried hydrogel of polysaccharide solid foam with a backing material; FIG. 3b shows an enlarged view of one corner of FIG. 3a.

FIG. 5b shows the top plan view of FIG. 5a.

DESCRIPTION

I. CHARACTERISTICS OF DRIED HYDROGEL OF HYDROPHILIC-HYGROSCOPIC POLYMER

Figure 4:
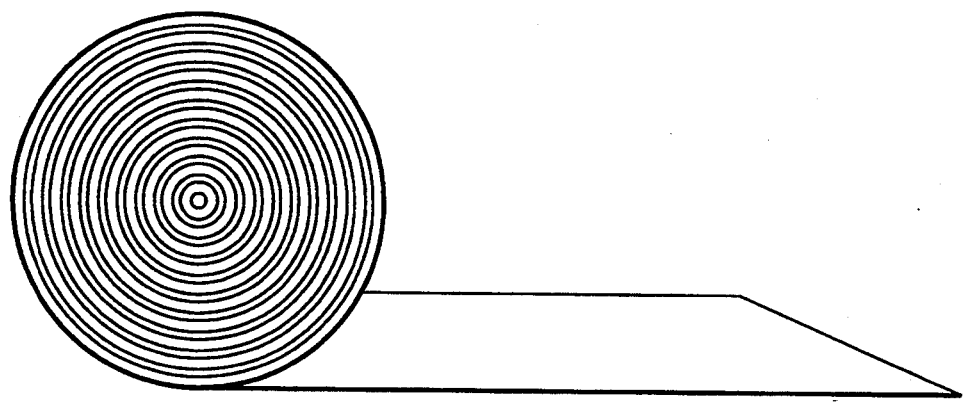
FIG. 4 shows a roll of freeze-dried hydrogel of polysaccharide solid foam.

The present invention relates to a therapeutic medical device, as classified by the FDA, comprised of a dried hydrogel of a hydrophilic-hygroscopic polymer.

A polymer, as used herein, means any molecule consisting of two or more monomeric units in the molecule.

Examples of hydrophilic-hygroscopic polymers include both unmodified and modified derivatives of: polymeric carbohydrates; polyacrylate; polyvinyl pyrrolidones; and others known to one skilled in the art.

Suitable polymeric carbohydrates include polysaccharides such as acemannan, konjac mannan (a glucomannan), guar gum (a galactomannan), heparin (an acid mucopolysaccharide), glucan and their modified analogs and derivatives. A variety of additional polysaccharides and/or their derivatives, modified or unmodified, may potentially be used as a base material for the dried polymeric saccharide solid foam such as alginates, carrageenan, chitin, ficoll, fructans, galactans, hydrophilic cellulose derivative, dextrans, glycogen, maltans, starch, glycosaminoglycans, gum arabic, karaya gum, lentinan, mannans, pectins, lipopolysaccharides, proteoglycans, proteochondroitin sulfates, sepharose, xylans, muramic acids, neuraminic acids, sialic acids, uronic acids, etc.

A hydrogel, as used herein, is a colloid in which the particles are in the external or dispersion phase and a liquid medium in the internal or dispersed phase. See FIG. 1. The liquid medium can be a polar solvent, such as water.

These hydrophilic-hygroscopic polymers, such as polymeric carbohydrates, can form hydrogels when dispersed as a colloid in a liquid medium, such as water. Hydrogels are complex lattices in which the dispersion media are trapped rather like water in a molecular sponge. Depending on the amount of the liquid medium present, the consistency of hydrogel can vary. Usually, the more liquid the medium is, the less viscous is the hydrogel. A hydrogel of an unmodified or modified polymeric carbohydrate is a colloid in which the polymeric carbohydrate particles are distributed throughout sufficient amount of a dispersed liquid medium, such as water, to form the colloid. Under certain conditions, a hydrogel of a polymeric carbohydrate may be dried without totally collapsing the arrangement or lattice of dispersed polymeric carbohydrate particles. For example, freeze-drying or lyophilizing which involves the rapid freezing of a hydrogel at a very low temperature followed by a "drying" by sublimation in a high vacuum gives a solid, yet flexible, polymeric carbohydrate foam that, with the absorption of additional fluid, can be transformed into a hydrogel.

The invention of a dried hydrogel of a hydrophilic-hygroscopic polymer in a solid foam physical state incorporates the attributes of a solid, yet flexible, therapeutic device that can be cut or formed to the shape of a wound or lesion. The solid foam material is in a lightweight cellular form having gas, such as air, bubbles dispersed throughout. In this physical solid foam form, a dried hydrogel can be prepared with non-covalently bound materials "trapped" within its interstices such that the solid foam can serve as a drug delivery system, hemostatic agent and biological response modifier.

If a dried hydrogel, in the form of a solid foam, is applied to a wound or lesion, excess fluid from the wound or lesion is absorbed by the solid foam, trapping potentially harmful wound exudate, and transforming the solid foam into a hydrogel at the surface interface of the covering and wound/lesion. The hydrogel provides a moist flexible wound/lesion covering that will retain contact with the wound or lesion and will not damage the underlying regenerating tissue. These physical events allow the wound or lesion to heal at an optimal rate.

Acemannan is an example of a carbohydrate polymer that can be formed into this solid foam of dried hydrogel, termed "freeze-dried or dried hydrogel of acemannan in solid foam form," "freeze-dried or dried acemannan solid foam," or "freeze-dried or dried acemannan hydrogel in solid foam form." The active substance of the aloe plant is acemannan. This substance has been shown to relieve pain and optimize healing. If the water is removed by freeze-drying from the hydrogel formed by a colloidal suspension of acemannan and other excipients in water, the resulting solid foam-like matrix of acemannan retains the same pain relief and healing properties. In this solid foam form, the acemannan can be cut, shaped, and formed into a large number of useful presentations such as dressing and bandages, hemostatic appliances, implants, etc.

Another property of the freeze-dried acemannan hydrogel in solid foam form is that it will absorb fluid from a wound or lesion. As it absorbs this fluid, it changes from the solid state back to a gel state. This absorption/gel formation process is a very beneficial medicinal event because potentially harmful exudate from a wound or lesion is absorbed by the foam and an optimally moist micro-environment is maintained at the lesion site.

In moist macro-environments, such as the mucous membranes of the mouth, respiratory and reproductive tract, the solid foam of acemannan will adhere to the lesion or wound and remain in place for periods of up to about one hour. Similarly, in a hemostatic application, the part of the pad of dried hydrogel of acemannan over the bleeding wound will absorb the blood and initiate coagulation while the surrounding gel pad will adhere to the surrounding organ surface and absorb additional fluid from the wound.

Pads of acemannan solid foam are self-adherent when wet and offer pain relief. Acemannan used in a topical form has no demonstrable toxicity and is completely biodegradable in the body. A major physical benefit of freeze-dried acemannan solid foam pads is that the healing and regenerating wound does not have to be disturbed during bandage change. One can directly apply another freeze-dried solid foam pad over the old one after inspection to monitor the healing progress. In fact the white freeze-dried hydrogel of acemannan in solid foam form turns into a gel or hydrogel upon absorption of a fluid. The resultant gel is transparent and allows for the visualization of the surface of the wound or lesion, allowing the practitioner to see the healing process beneath the gel covering.

Freeze-dried acemannan in solid foam pad form can also serve as a delivery agent or as a hemostatic agent. It can be made preservative-free with an extended shelf life when sterilized by gas or radiation and protected from contamination and moisture. Dried foam pads of acemannan can easily be shaped to fit the individual wound, and by forming a gel upon contact with liquid or body fluids, the gel serves to protect the wound or lesion from contamination by its environment. With this protection, the wound or lesion will heal at the optimal rate, which has been shown to be faster than that for untreated or treated controls in animal and human studies.

II. MANUFACTURING DRIED HYDROGEL OF HYDROPHILIC-HYGROSCOPIC POLYMER

A. Manufacturing Process

In one aspect, the manufacturing process involves preparing a hydrogel of a hydrophilic-hygroscopic polymer, such as a polymeric carbohydrate, in a liquid medium, such as water or other polar solvent, and then removing the liquid medium from that hydrogel to form a dried hydrogel of hydrophilic-hygroscopic polymer in solid foam form that can be cut, packaged, sterilized and stored for testing or clinical use. Upon contact with a liquid, such as water, the dried hydrogel foam will convert back to a hydrogel.

The first step in one manufacturing process involves combining the desired initial polymeric carbohydrate, such as powdery acemannan, in a medium, such as water, such that a colloid of carbohydrate dispersion (hydrogel) is formed.

A mixture of an appropriate polymeric carbohydrate and water can form a hydrogel, and the proportions of one embodiment are illustrated in Table 1.

Then, the hydrogel of the polymeric carbohydrate are dehydrated to give the dried hydrogel of a polymeric carbohydrate in solid foam form. Preferably, the dehydration is accomplished by freeze-drying. Conventional solid-drying equipment and heat-transfer equipment, as described in Perry's Chemical Engineers' Handbook (Sixth Edition), may be used.

The final texture and density of the dried solid foam of hydrophilic-hygroscopic polymer is dependent on the amount of water that is in the starting hydrogel. The more water is included in the interstices of the hydrogel, the more porous with lower density the dried solid foam will be. Generally, water content in a dried solid ranges from about 5% to about 15% by weight, preferably from about 8% to about 12% by weight, and more preferably about 10% by weight.

TABLE 1

| Formula of Hydrogel of Acemannan | |
|---|---|
| INGREDIENT | FORMULA (W/W %) |
| Purified water | 99.40 |
| Acemannan* | 0.60 |

*May be substituted for with a glucomannan, a galactomannan, or a glucan.

A preferred embodiment of a polysaccharide dispersion mixture, its ingredients and their proportions, is given in Table 2. The preparation of the dispersion mixture was initiated by mixing the benzethonium chloride with povidone (International Specialty Products, Wayne, N.J.) and water until all of the components were completely dispersed. The hydrogen peroxide was then added, followed with the sifting in of the acemannan powder with mixing. Once the acemannan was dispersed, hydroxyethylcellulose (Aqualon, Hopewell, Va.) was then slowly sifted into the mixture with the mixing continued until all components were well dispersed.

TABLE 2

| Ingredients of Preferred Hydrogel of Acemannan | |
|---|---|
| INGREDIENT[1] | W/W % |
| Purified water | 98.88 |
| Plasdone[2] | 0.5 |
| Benzethonium chloride[3] | 0.002 |
| Hydrogen peroxide 35% | 0.13 |
| Acemannan | 0.05 |
| Natrasol 250H, U.S.P.[4] | 0.445 | pH adjusted with sodium hydroxide to between 6–6.5.
[1]Additional ingredients may include antibiotics such as tetracycline, oxytetracycline, gentamycin; metal ions such as zinc, cobalt, iron and manganese; biologics such as BMP hormone and growth factors; drugs such as chemotherapeutic agents, including anticancer agents, antiviral agents, antifungal agents, nucleosides, nucleotides, and steroids; topical anesthetics; vaccines, such as killed viruses, modified live viruses, and viral components; and hematological agents.
[2]Povidone, International Specialty Products, Wayne, New Jersey.
[3]Benzethonium chloride may be excluded for a preservative-free product. If desirable, other preservatives, such as methylparaben may be added.
[4]Hydroxyethylcellulose, Aqualon, Hopewell, Virginia.

Only acemannan meeting appropriate quality control specifications was used in the dispersion mixture. The specifications of the acemannan powder are given in Table 3 and are used to confirm the purity of the added acemannan.

Because of its chemical properties, acemannan (or other polysaccharides) can form non-covalent bonds with a wide variety of other ingredients or excipients including pharmaceutical products. Freeze drying these mixtures in the presence of the hydrogel of polymeric carbohydrate will produce a drug delivery vehicle for delivery of the ingredients to the desired site. Examples of ingredients that may be added to the mixture during preparation include antibiotics (e.g., tetracycline, oxytetracycline, or gentomycin), metal ions (e.g., Zn, Co, Fe and Mn), biologics (e.g., hormones, and growth factors), or drugs (e.g., chemotherapeutic agents, including anticancer agents, antiviral agents, and antifungal agents, nucleosides, nucleotides, steroids, topical anesthetics, and hemostatic agents). A microorganism can also be added during the preparation of dried hydrogel of a hydrophilic-hygroscopic polymer, such as freeze-dried acemannan solid foam. Examples of microorganism include a vaccine, such as bacteria, fungus, protozoa, yeast, microplasma, and virus, each of which can be either killed, attenuated ("life-modified"), or components or particles thereof.

In addition, benzethonium chloride may be excluded from the mixture to produce a preservative-free product. It is not necessary to include a preservative as the resulting dried hydrogel of polysaccharide solid foam is easily sterilized by gas or radiation, such as ultraviolet light and heat. In preferred embodiments, the preservatives will be excluded, as preservatives may dehydrate the wound or lesion, sting the patient, and/or inhibit the optimal cellular growth of new tissue.

After quality control testing, the mixture was heated to approximately 45° C. The temperature was then adjusted to 35° C. The pH of the mixture was adjusted to 6.5 with 0.1N sodium hydroxide and then transferred to lyophilizer trays to a depth about one-eighth inch as illustrated in FIG. 2.

TABLE 3

| Specifications of Starting Acemannan Powder | |
|---|---|
| Appearance | Amorphous powder |
| Identification | Conforms to IR reference spectrum; conforms to TGA reference thermogram |
| Water content | Not more than 10% |
| Residue on Ignition | Not more than 6% |
| Microbiological | Average aerobic plate count not to exceed 200 cfu/ml in a 0.1% solution; No Gram negatives; No obligate anaerobes; No S. aureua |
| Acemannan content | Not less than 73% |
| Molecular weight Distribution of Acemannan | 73% of acemannan material between 10,000 and 1,000,000 Daltons |

Figure 5B:
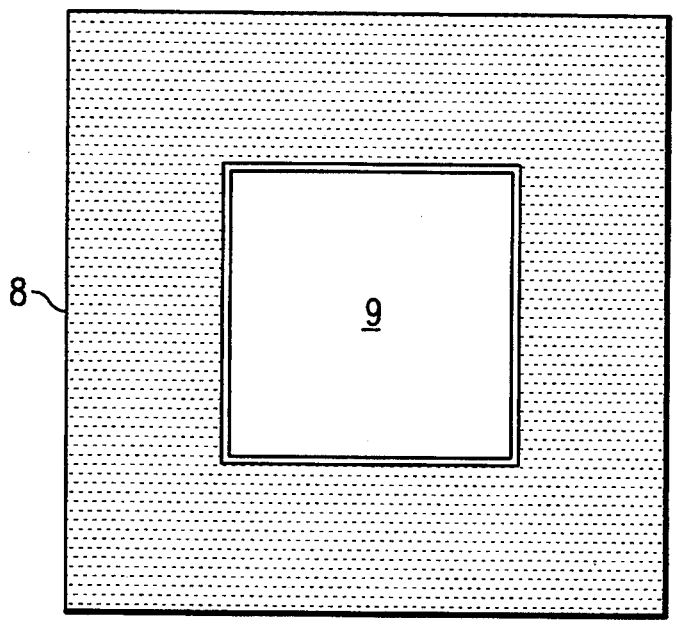
Figure 5A:
FIG. 5a shows a freeze-dried hydrogel of polysaccharide solid foam with an adhesive "bandage" backing.
Figure 6:
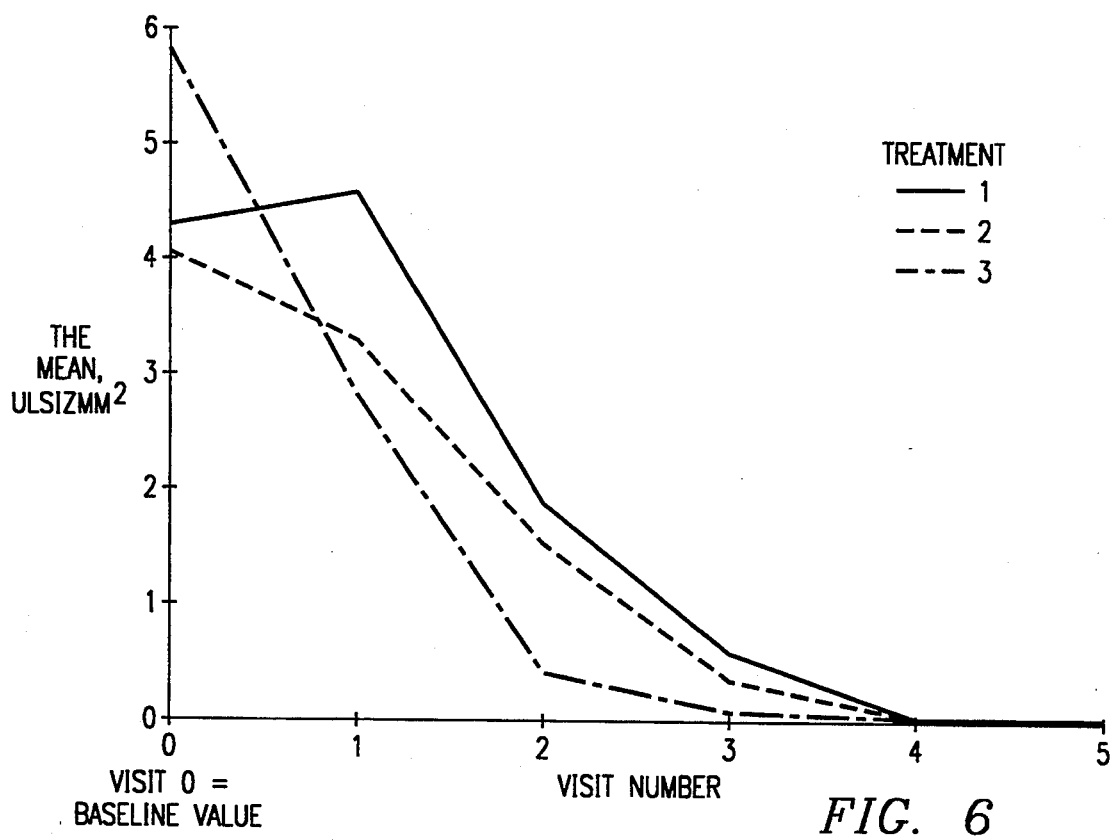
FIG. 6 shows the mean lesion size in the three treatment groups with visit number.
Figure 7:
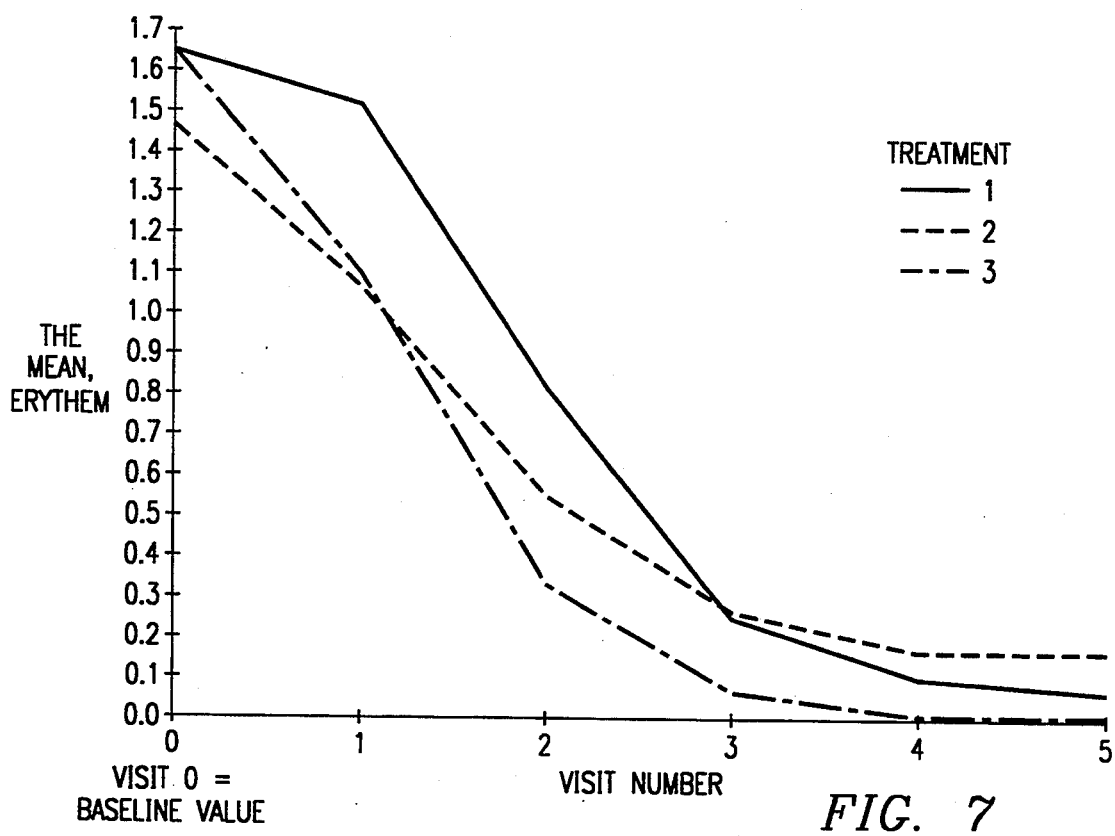
FIG. 7 shows the mean lesion erythema in the three treatment groups with visit number.
Figure 8:
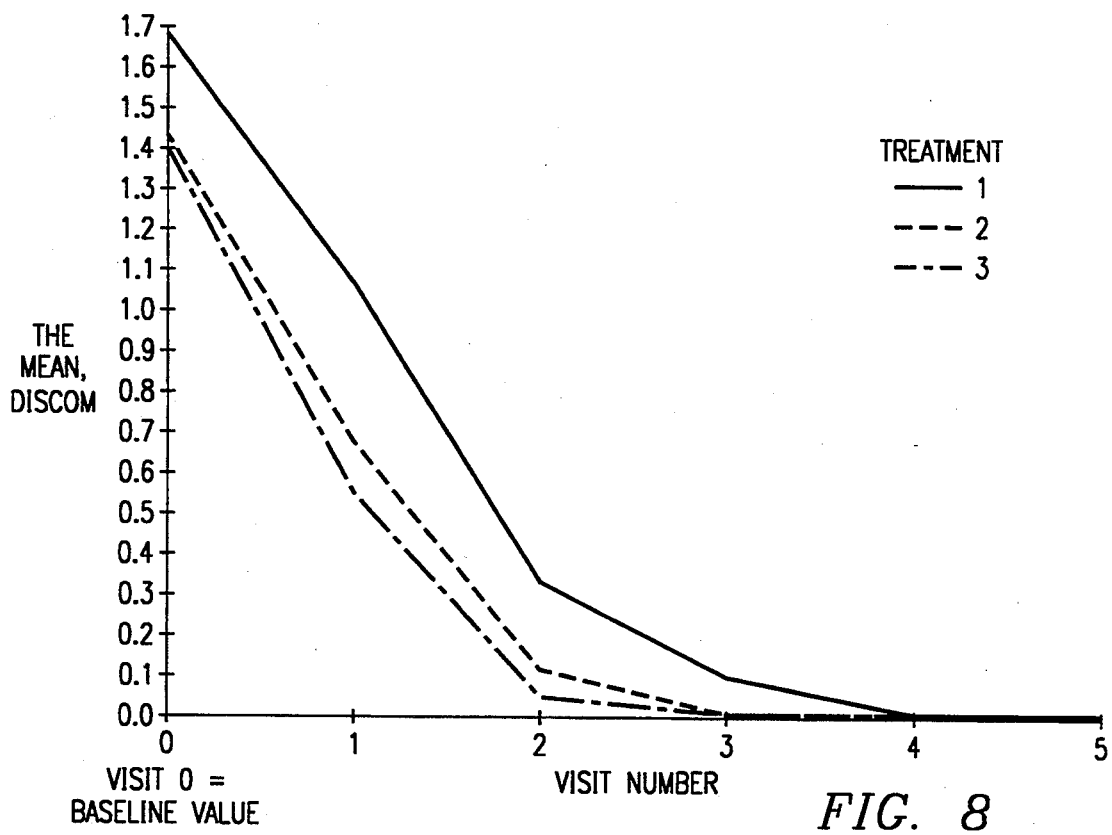
FIG. 8 shows the mean patient discomfort in the three treatment groups with visit number.
Figure 9:
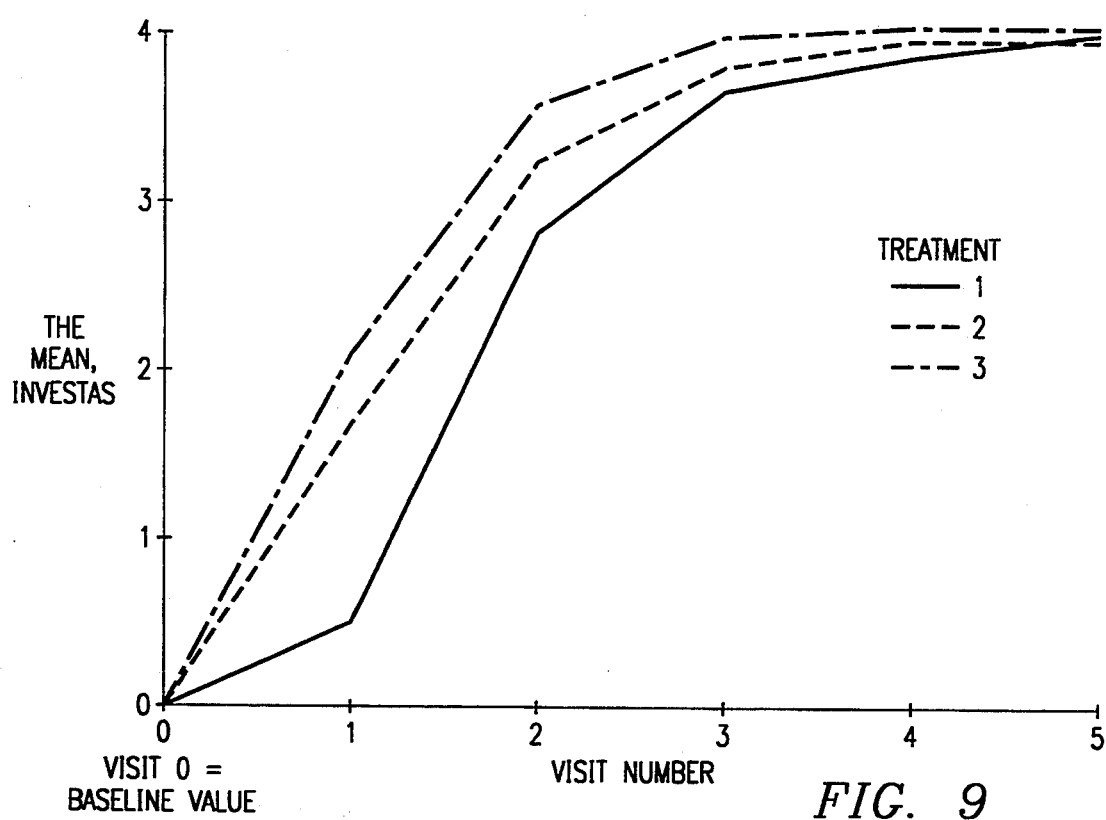
FIG. 9 shows the mean of the investigator's graded impression of clinical improvement in the three treatment groups with visit number.
Figure 10:
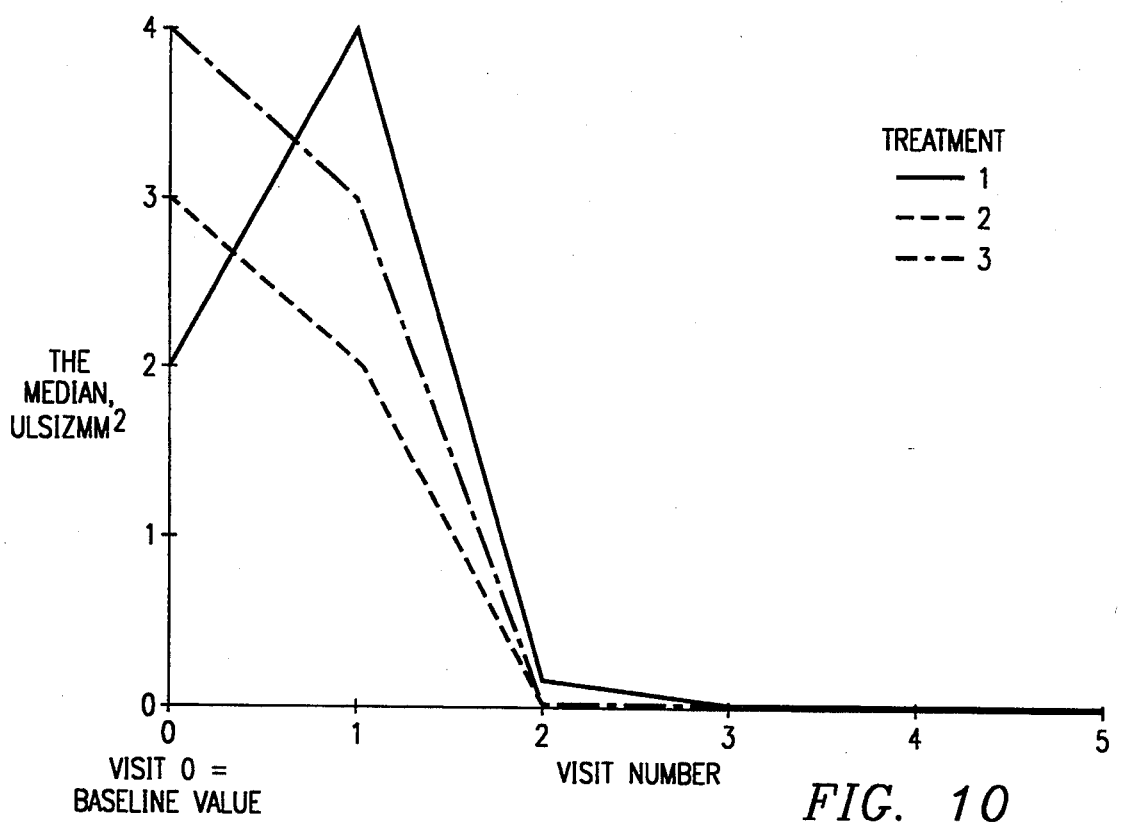
FIG. 10 shows the median lesion size in the three treatment groups with visit number.
Figure 11:
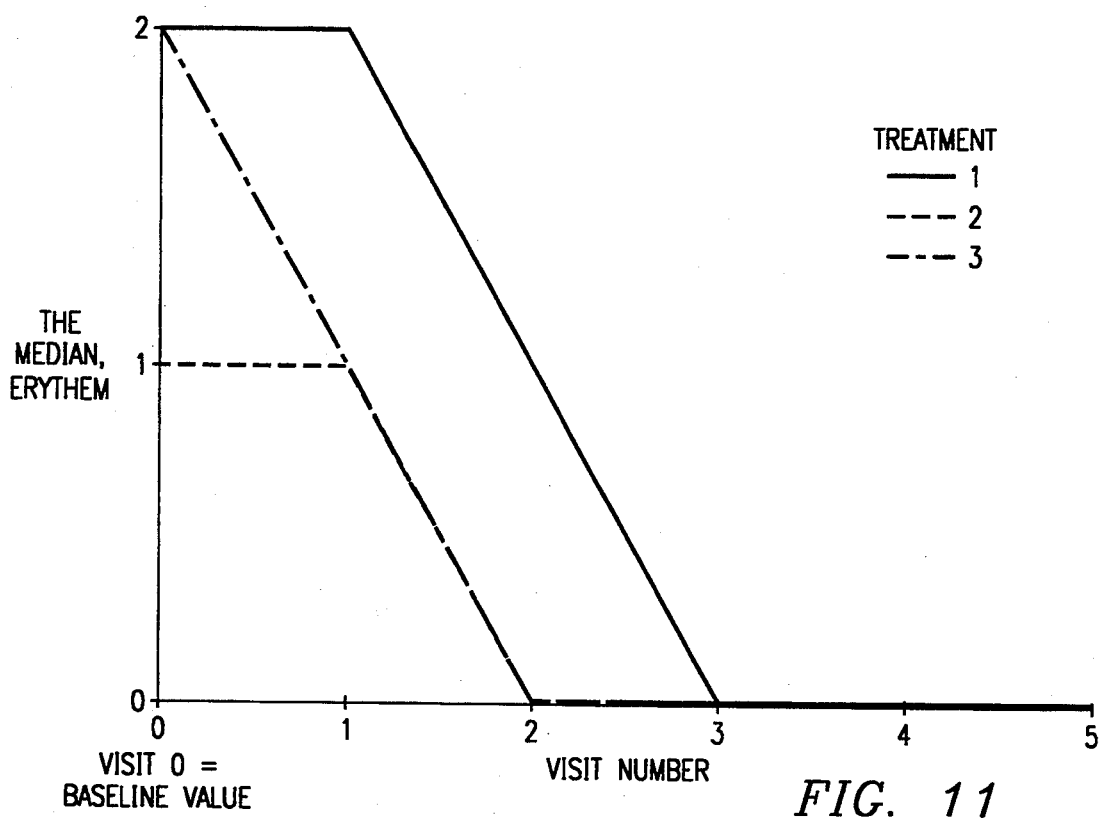
FIG. 11 shows the median lesion erythema in the three treatment groups with visit number.
Figure 12:
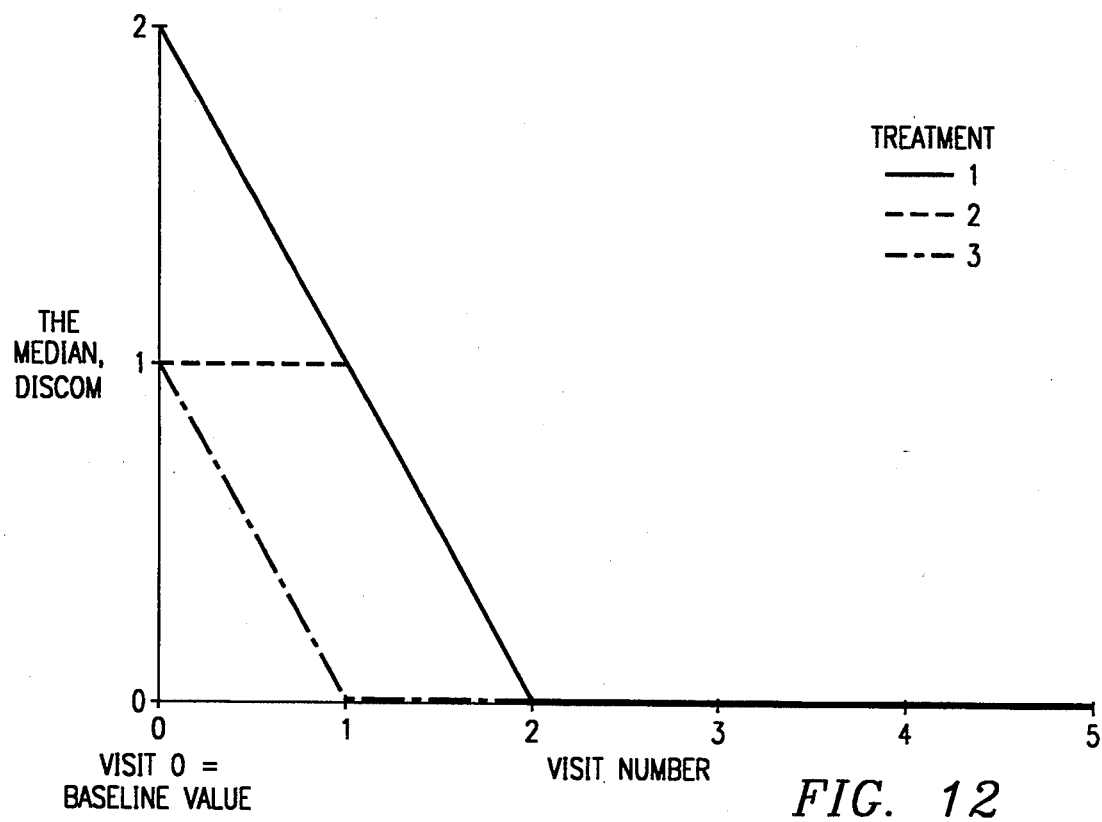
FIG. 12 shows the median patient discomfort in the three treatment groups with visit number.
Figure 13:
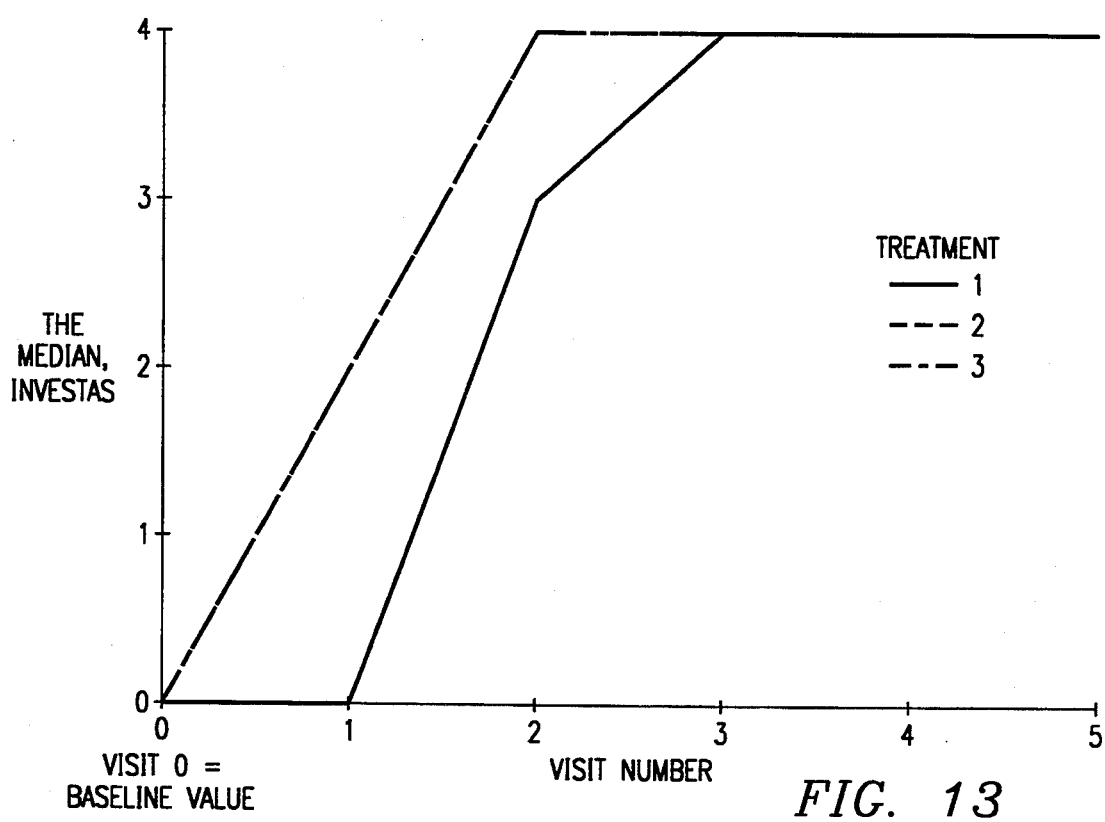
FIG. 13 shows the median of the investigator's graded impression of clinical improvement in the three treatment groups with visit number.

The polysaccharide dispersion mixture may be poured into the lyophilizer tray and freeze-dried to form a white cotton-like solid foam that can be directly applied to a trauma site. Alternatively, the mixture may be poured into the lyophilizer tray, 1, over a backing material as shown in FIG. 2. If the hydrogel 3 is freeze-dried on top of a backing material 2, the freeze-dried product will be an acemannan solid foam wound dressing 4. The backing material can be varied to adjust porosity, density, gas and liquid permeability to produce an appropriate wound dressing for different types of wounds. This two-layered wound dressing, 4, shown in exploded view in FIG. 3b of FIG. 3a where A denotes freeze-dried hydrogel of acemannan and B indicates a backing material may be produced in sheets or rolls as illustrated in FIG. 4. The freeze-dried hydrogel of acemannan adheres to the porous side of rolled up sheet. The back of the porous side is non-porous and will not stick to the freeze-dried hydrogel when rolled up. The hydrogel of acemannan, 9, may be lyophilized such that it adheres to the central portion of an adhesive bandage, 8, as seen in FIGS. 5a–b.

Tight environmental control must be maintained during freezing to prevent layering out of the components. Temperature of the freeze-drying chamber was lowered incrementally. In a 4.8 sq. ft. shelf of freeze dryer, it took about 3-4 hours to lower the temperature from room temperature to freezing point. About 25-30 g. of freeze-dried hydrogel of acemannan was obtained from about 3.5 l of hydrogel of acemannan as given in Table 2. The final product could then be cut into the appropriate shapes and sizes with samples collected for in-process testing.

After quality control testing, the freeze-dried solid foam of acemannan product (as described below in Section B), was approved for unit component packaging. Terminal sterilization could be accomplished by gas, radiation, such as dry heat, and UV light. The preferred method was radiation. Once final product packaging and testing was completed, samples were retained for long-term stability studies.

B. Quality Control For Freeze-Dried Hydrogel of Acemannan Solid Foam

Every lot of final product was tested by the specific methods described below, and acceptable product will meet the specifications given in Table 4, as illustrated in Table 5 for Lots #1 and #2.

1. Appearance. The product should form a white, porous, flexible, medium-soft layer. It should be white to off-white and of uniform composition. Lots with deviations from this criteria were rejected. Added ingredients may change the appearance slightly and were accounted for during visual inspection.

2. pH. In the presence of water, the acceptable pH range of the freeze-dried hydrogel of acemannan was 6.0 to 7.5. Prior to pH measurement, meters were calibrated against standard pH buffers.

3. Thermogravimetric Analysis. The content of water, and ash residue (calcium and magnesium oxide of calcium oxalate and magnesium lactate, other salts, Natrasol residue, etc.) were determined by thermogravimetric analysis as a single experimental procedure. The method was very accurate with instrumental variability of within 0.5 percent. The instrument utilized by the quality control group was a Mettler TA 3500 Thermogravimetric Analyzer with TG 50 Thermobalance, TC 10A controller, and IBM PC data system. A 10 milligram sample was introduced into the system and the following temperature program was followed: the sample was heated from 2° C. to 600° C. at a rate of 20° C. per minute in an inert nitrogen gas atmosphere, and then to 780° C. under oxidizing conditions. The sample was left at this temperature for 2 minutes. All gases were maintained at a flow of 200 ml per minute. When the analysis was finished, the data system printed out the real time and the derivative of the weight loss versus temperature, and the corresponding percentages of each peak. This method has been validated and standardized.

4. Microbiological Assay. The microbiological specifications for this product required that microbiological contamination be less than 100 colony forming units per ml. The product must not contain *E. coli, Ps. aeruginosa, S. aureus,* or *Salmonella sp.* (fever causing bacteria).

Testing was done by sampling the product under a laminar flow hood and applying those samples to specific growth media, leading to the identification of any organism that grew out. Media used to plate the samples on included tryptic soy broth, fluid thioglycollate medium, fluid lactose medium, tryptic soy agar (TSA) plates, and Sabouraud dextrose agar plates with chloramphenicol. The TSA plates were also incubated anaerobically.

5. Bacteria Inhibition Testing. Inhibition testing was done utilizing clinical lot #2 (described in Table 5) with the bacteria *Streptococcus salivarius* and *Streptococcus sanguis* on tryptic soy agar and blood agar plates. After incubation at 35° C. for 72 hours, the zone of "no growth" around the product was measured and recorded. Not every lot of product was tested by this method.

6. Size Exclusion Chromatography. The molecular weight distribution for each lot of freeze-dried acemannan solid foam used was determined by exclusion HPLC using a Waters HPLC system with a 590 pump module, WISP 712 Autosampler, 410 differential refractometer detector, Spectra-Physics 4290 integrator and a Chromstation AT data system. Pullulan's standards of known molecular weights and their retention times were used to determine the relative molecular weights of all sample peaks. The sums of the areas of all acemannan sample peaks that occurred before the calculated 10,000 Daltons retention time was recorded. Results are recorded as the percent of material greater than 10,000 Daltons. The acemannan used for dried foam manufacturing should preferably contain at least 73% of material having greater than 10,000 Daltons.

TABLE 4

Specifications of Different Lots of Freeze-Dried Acemannan Hydrogel in Solid Foam Form

| TEST | SPECIFICATION | REFERENCE |
|---|---|---|
| Appearance | White cotton-like | SCP #2001 |
| pH | 6.0–7.5 | SCP #2014 |
| Water content | Not more than 10% | SCP #2003 |
| Residue on ignition | Not more than 3% | SCP #2003 |
| Microbiological | Less than 100 cfu/ml (Free of E.coli, Ps. aeruginosa, S.aureus and Salmonella sp.) | SCP #13,675 |

TABLE 5

Quality Control Results

| TEST | REFERENCE | RESULTS | |
|---|---|---|---|
| Clinical lot # | | Lot #1 | Lot #2 |
| Appearance | SCP #2001 | passed | passed |
| pH | SCP #2014 | 6.14 | 6.47 |
| Water Content | SCP #2003 | 7.33% | 10.78% |
| Residue on Ignition | SCP #2003 | 1.23% | 0.66% |
| Microbiological | SCP #13,675 | passed | passed |

7. Determination of Densities. The solid acemannan foam was carefully cut into rectangular cubes. The length, width and thickness were measured with a micrometer (Mitutoyo Corporation, Minato-ku, Tokyo, Japan) graduated in 0.01 mm units to obtain the volume of the cube in cubic centimeters (cc). The weight of the cube was determined using an analytical balance. The density was calculated from the weight and volume of the cube in grams per cubic centimeter (g/cc).

For foam of one embodiment, the mean density with 95% confidence limit was calculated as $0.024 \pm 0.007$ g/cc (n=18). The upper limit density $0.033 \pm 0.007$ g/cc (n=12) was determined using a hydrogel gel of acemannan freeze-dried at less than optimal conditions.

The density of freeze-dried hydrogel of acemannan solid foam of another embodiment was calculated to be $0.0032 \pm 0.0007$ g/cc (n=3). This density was determined by measuring the diameter and thickness of the foamlike disc while still in the bottle. This was necessary because the disc collapses on exposure to air.

The measured diameter and thickness furnished the volume ($90 \, r^2 \, h$) of the disc. The weight was subsequently determined with analytical balance and the density calculated by dividing the weight of the disc by the volume.

Thus, the density of the freeze-dried hydrogel of acemannan solid foam could range from about 0.003 g/cc to about 0.033 g/cc. Preferably, the range should be from about 0.02 g/cc to about 0.03 g/cc.

III. USES OF DRIED HYDROGEL OF HYDROPHILIC-HYGROSCOPIC POLYMERS

Polysaccharide solid foam is a freeze-dried polysaccharide hydrogel that can be used for the protective management of wounds and lesions, including ulcers. The solid foam product is classified as a medical device and contains a non-toxic, biodegradable polysaccharide. The device of the present invention is self-adherent and will remain in contact with the target site for a relatively extended period of time.

An acemannan solid foam is composed primarily of acemannan and 5–15% water. A preferred embodiment contains 8–12% water and the most preferred embodiment contains about 10% water.

Acemannan consists of long-chain polydispersed β-(1,4)-linked mannan polymers interspersed with O-acetyl groups. In both animal and human studies acemannan has been shown to be a potent immunomodulator, and anti-infective agent. The application of a freeze-dried hydrogel of acemannan solid foam to the wound or lesion site can deliver increased concentrations of acemannan to the trauma site and enhance healing.

In acute and subacute animal studies using parenterally administered acemannan in animals, virtually no systemic toxicity was seen at doses up to 80 milligrams per kilogram. Studies in healthy human and animal have also shown acemannan to be virtually nontoxic when administered orally or topically.

The freeze-dried polysaccharide solid foam device may be of use on a large variety of wounds or lesions to ensure that they remain moist, free of infection, and undisturbed by dressing changes. In animals, freeze-dried polysaccharide solid foam may be of use to absorb wound exudate in the treatment of abscesses, fistulas, moist dermatitis, and eczema. The present invention may also be of use to treat dry wounds that require a sterile material that can cover large areas. The described polysaccharide solid foam can be reconstituted with saline or other suitable therapeutic liquid or suspension to form a moist gel that can be applied to burns, abrasions, and incisional wounds.

For example, full-thickness thermal wounds in guinea pigs treated with Cartington Dermal Wound Gel (CDWG), containing Aloe vera gel, healed in an average of 30 days. Wounds treated with silver sulfadiazine (Silvadene) required an average of 47 days to heal, while those treated with plain gauze dressings healed in an average of 50 days [Rodriguez-Bigas et al., "Comparative Evaluation of Aloe vera in the Management of Burn Wounds in Guinea Pigs," *Plastic and Reconstructive Surgery*, vol. 81, no. 3, pp. 386–89 (1988)].

In humans, the present invention may be of use to treat cuts, abrasions, post-operative wounds, burns, ulcers, dermatitis, diaper rash, skin irritations, and other types of tissue trauma. Cartington Dermal Wound Gel (CDWG) containing acemannan was found to enhance the healing rate of partial-thickness dermal wounds in male volunteers by 45%, as compared to treatment with a gauze dressing alone. Freeze-dried acemannan solid foam would be expected to have at least the same effectiveness in wound healing as CDWG, while providing certain advantages. The present invention may be particularly useful in a variety of dental applications.

For example, the immune stimulatory activity of a dried hydrogel of acemannan solid foam should be helpful in combating oral fungal, bacterial and vital infections. It has been shown that freeze-dried hydrogel of acemannan in solid foam form is effective in the treatment of Herpes labialis (fever blisters) caused by the herpes simplex virus.

Herpes labialis occurs in approximately 20–30% of the population and is characterized by lesions of the buccal or labial mucosa.

Freeze-dried acemannan solid foam may also be of use to treat oral burns and neoplasia considering acemannan's documented immune enhancing and antitumor activity. In addition, dried acemannan solid foam may be useful as packing and/or dressing after periodontal surgery, tooth extraction, dental implants, or dental biopsy.

Recently completed studies have shown the effectiveness of freeze-dried acemannan solid foam in the treatment of recurrent aphthous ulcers as described in Example 1.

Recurrent aphthous ulcers (RAUs), also known as canker sores, occur in approximately 15–20% of the population and can be a source of a great deal of discomfort. While many patients experience only occasional outbreaks of isolated ulcerations, others suffer from continuous lesions that severely affect their quality of life. Recurrent minor aphthous ulcerations involve only the mucosa and do not affect the deeper layers of the oral tissues. They heal by mucosal regeneration, usually in 7–14 days, without scar formation.

A variety of products have been evaluated for their therapeutic effectiveness in the management of recurrent minor aphthae, but few adequately documented, reproducible studies have been done that demonstrate the efficacy of any particular product. Products that contain topical anesthetics or that provide protection from the oral environment are the most common treatments. However, some of these products have a disagreeable taste or texture, and others may sting the patient upon application. In addition, some products that are designed to adhere to and protect the affected tissue from the oral environment consist of more than 80% alcohol, and thus are more likely to desiccate and further damage the tissues than to ensure a moist environment suitable for proper healing.

Hydrogels are ideal agents for providing a moist environment necessary for optimal wound healing. A hydrogel that protects ulcerated tissues from the oral environment and simultaneously allows adequate hydration could serve to hasten the healing process of oral mucosal ulcers.

The dried acemannan hydrogel in fluffy solid foam form adhered to the oral mucosa upon contact, slowly rehydrated to a gel and remained in place for up to about one hour. A pilot study was designed to determine whether this product affected the healing process of recurrent aphthous ulcers.

EXAMPLE 1

A cat with a vascular necrosis was treated with the therapeutic device of freeze-dried hydrogel of acemannan in solid foam form having a "bandage" backing. The device was applied to severely damages areas of tarsus/metatarsus. After overnight with first application of the therapeutic device, there was a dramatic reduction in swelling, and very little skin sloughing occurred. The wound healed significantly after three consecutive applications, about 24 hours apart, of the therapeutic device. The cat was then discharged from the clinic.

EXAMPLE 2

A clinical study was designed to determine the effectiveness of Orabase TM, acemannan hydrogel, and freeze-dried acemannan hydrogel in solid foam form in the treatment of recurrent aphthous ulcers by monitoring the time necessary for complete healing to occur.

Initially a double-blind, randomized study of 60 volunteer patients with a history of recurrent aphthous ulcers, having at least one lesion of less than 48 hours, was performed. Patients were randomized to one of two groups based on a table of random numbers. Group I consisted of 30 patients treated with Orabase TM, a plasticized gel and guar manufactured by Colgate-Hoyt Laboratories. Group II consisted of 30 patients treated with acemannan hydrogel, at a 0.1% concentration of acemannan in a gel vehicle with methylparaben and benzethonium chloride added as preservatives.

Subsequently an open-label study involving 25 volunteer patients was initiated. These patients (Group III) were treated with freeze-dried hydrogel of acemannan solid foam using the same protocol used in the treatment of Groups I and II.

Each volunteer patient applied the appropriate treatment to his/her lesion four times a day until the lesion was healed. The patient was clinically evaluated every 3 days throughout his/her treatment. Clinical evaluation consisted of determining lesion size, degree of erythema, severity of pain and the investigator's impression of clinical improvement.

TEST ARTICLE

A. Group I: Orabase ® was supplied in a properly labeled 0.17 oz tube. Orabase ® is comprised of plasticized gel and guar.

B. Group II: Acemannan hydrogel was supplied in a 0.5 oz tube, containing about 0.1% acemannan.

C. Group III: Freeze-dried acemannan hydrogel in solid foam form was supplied to the patient in a properly labeled glass jar containing 60 "pledgets" of test article. Each pledget was approximately 1 cm². Freeze-dried acemannan hydrogel in solid foam form was prepared from mixture comprised of ingredients as appear in Table 2.

Selection of Volunteer Patients

Selected volunteers were at least 18 years old with a positive history of recurrent minor aphthae. Volunteers of either sex were in good general health, but had at least one aphthous lesion of less than 48 hours duration on the buccal or labial mucosa, soft palate or floor of the mouth.

Volunteers were excluded from the study if they demonstrated a history of sensitivity to Aloe vera or any other ingredient in the test article. Volunteers were also rejected if they had: topically applied any medication to the affected area during the previous 2 weeks; orthodontic devices such as braces, brackets or retainers; dental surgery within the previous 1 month; systemic steroid use during the previous 1 month; antibiotic use during the previous 2 weeks; a positive history of systemic diseases that may manifest as recurrent oral ulcerations such as Behcet's disease, Crohn's disease, ulcerative colitis, anemia, etc.; non-steroidal use within the last 48 hours; or current drug or alcohol abuse. Pregnant volunteers were also excluded from the study.

Protocol

A. Pretreatment procedures:

1. The investigator obtained a signed informed consent form from the patient before admitting him/her to the study.
2. The volunteer was screened to confirm the existence of at least one minor aphthous ulcer of less than 48 hours duration. Ulcers, by definition, were located on the buccal or labial mucosa, soft palate or floor of the mouth. Demographic data as well as a complete medical history were obtained. Current medications, including those taken within the previous 30 days, were recorded.
3. The patient's history of recurrent aphthae was verified by recording a fully detailed evaluation of the patient's oral ulceration experiences. Data obtained included:
   (a) Provocative agents;
   (b) Average number of aphthae per year;
   (c) Average number of aphthae per outbreak;
   (d) Average length of time for healing; and
   (e) Therapeutic modalities utilized by the patient.
4. The initial lesion size was measured with the use of a sterile ruler graduated in 1-mm increments. The maximum width of the lesion in both a horizontal and vertical direction was recorded. Degree of erythema associated with the lesion was recorded using a scale from 0–3, wherein 0=none, 1=mild erythema, 2=moderate erythema, and 3=severe erythema.
5. Degree of patient discomfort was categorized by the patient using a scale from 0–3, wherein 0=no pain, 1=mild pain, 2=moderate pain, and 3=severe pain.
6. Once a patient was admitted into the study he/she was given the test article with instructions on proper application. The patient was instructed to apply the agent topically to the identified lesion four times each day following meals and oral hygiene procedures. He/she was given a patient diary and instructed to enter the time of each application of test article. In addition, he/she categorized and entered into the patient diary the degree of discomfort experienced immediately after test article administration, and overall degree of discomfort experienced that day, using the grading scale described above. The patient returned with the patient's diary every 3 days until the identified lesion was completely healed.

B. Evaluation visits:

The following was performed at each evaluation visit:

1. The investigator reviewed the patient's diary with the patient.
2. Lesion size was measured as in the pretreatment evaluation.
3. Degree of erythema was determined utilizing the grading scale described above.
4. The investigator's assessment of the overall improvement of the lesion was recorded using the following scale:
   - 4 Ulcer completely healed
   - 3 Marked improvement
   - 2 Moderate improvement
   - 1 Slight improvement
   - 0 Ulcer unchanged
   - −1 Ulcer worsened
5. On the visit where it was determined that complete healing had occurred, the investigator collected all test article and the patient diary. The patient was asked for comments regarding medication as well as the testing procedure in general.

Statistical Analysis

The data consisted of information collected through May 17, 1993, from case report forms for 30 patients treated with Orabase ™, 30 patients treated with acemannan hydrogel, and 25 patients treated with freeze-dried acemannan in solid foam form. Data used in the analyses included overall patient discomfort, pre- and post-application discomfort for each application of acemannan, and the time that the freeze-dried acemannan solid foam remained in the mouth as reported in the patient diary. In addition, the data included the results of the clinical evaluations (i.e., discomfort, degree of erythema, investigator's assessment, and ulcer size as reported on the clinical grading scores sheet).

Healing time was computed by subtracting the date of the first visit from the date of the last visit. In order to "balance" the data, the last data values for each patient were carried forward to obtain clinical grading data for five visits and diary data for fifteen days.

The mean, standard deviation, and range was computed for healing time by treatment. An analysis of variance (ANOVA) was used to determine if the healing time was significantly different for the three treatment groups. If significant differences among the treatment groups were found, Fisher's LSD was used to identify where the differences occurred. The mean, standard deviation, range, and sample size for the remaining variables listed were calculated and tabulated by visit number and treatment. ANOVAs were performed to investigate differences among treatment groups at each time point; the corresponding nonparametric tests were also performed. Significant differences were investigated using Fisher's LSD.

The average healing time for patients treated with freeze-dried acemannan solid foam (treatment group 3) was 5.8 days compared to an average of 7.96 for group 1 and an average of 5.89 for group 2. This difference is statistically significant ($p=0.0028$). Paired comparisons showed significance is due to differences between groups 1 and 2 and between groups 1 and 3.

Graphs displaying the mean and median values of ulcer size, erythema, discomfort, and investigator's assessment at each visit are found in FIGS. 6 to 13. Statistically significant differences were found at visit 1 for erythema ($p=0.0526$ ANOVA, $p=0.0519$ Kruskal-Wallis), for investigator's assessment ($p=0.0021$ ANOVA, $p=0.0027$ KW), discomfort ($p=0.0508$ ANOVA, $p=0.0516$ KW), and for ulcer size ($p=0.0494$ KW). Significance was due to differences between groups 1 and 2 and between groups 1 and 3 in cases except discomfort where the only difference was between groups 1 and 3. No other significant differences were found for clinical grading data.

In the patients' diaries, patients reported that the freeze-dried acemannan solid foam remained in the mouth an average of 48.24 minutes (SD 17.22). The average change in discomfort score immediately prior to and 2 minutes after the application of acemannan foam was 0.9762. The difference was statistically significant ($p=0.0001$) and indicates an improvement in discomfort experienced. In addition to recording discomfort immediately prior to and following treatment, patients recorded overall discomfort on a daily basis. There were no differences in overall discomfort as reported in the diary.

This study demonstrates that freeze-dried acemannan solid foam is effective in the management of aphthous ulcers. As compared to the group treated with Orabase ®, healing time was reduced by 27%. Additionally, patients reported a significant decrease in discomfort after treatment with freeze-dried acemannan solid foam.

Although the present invention and its advantages have been described in detail, it should be appreciated by those skilled in the art that the conception and the specific embodiments disclosed may be readily utilized as a basis for modifying or designing other compositions and structures for carrying out the same purposes of the present invention. It should also be realized by those skilled in the art that such equivalent constructions do not depart from the spirit and scope of the invention as set forth in the appended claims.

What is claimed is:

1. A therapeutic device comprising a dried hydrogel in the form of a flexible solid foam that can be cut to the shape of a wound or lesion, said therapeutic device having gas bubbles dispersed throughout and being prepared by removing a liquid medium from a hydrogel, said hydrogel comprising particles of a hydrophilic-hygroscopic therapeutic polysaccharide dispersed in said liquid medium, wherein said therapeutic polysaccharide is obtained from aloe vera, said therapeutic device being capable of being transformed into said hydrogel upon absorption of additional liquid medium.

2. The therapeutic device as in claim 1, wherein said liquid medium comprises a polar solvent.

3. The therapeutic device as in claim 1, wherein said liquid medium comprises water.

4. The therapeutic device as in claim 1, wherein said liquid medium is removed from said hydrogel by freeze drying.

5. The therapeutic device as in claim 1, wherein said hydrophilic-hygroscopic therapeutic polysaccharide obtained from aloe vera comprises acemannan.

6. The therapeutic device of claim 1, wherein said liquid medium comprises from about 5% to about 15% by weight of said therapeutic device.

7. The therapeutic device of claim 1, wherein said hydrophilic-hygroscopic therapeutic polysaccharide comprises from about 85% to about 95% by weight of said therapeutic device.

8. The therapeutic device of claim 1, wherein said therapeutic device has a density of from about 0.002 g/cc to about 0.04 g/cc.

9. The therapeutic device of claim 1, wherein said therapeutic device has a density of from about 0.02 g/cc to about 0.03 g/cc.

10. The therapeutic device as in claim 1, further comprising an antibiotic.

11. The therapeutic device as in claim 10, wherein said antibiotic is selected from the group consisting of tetracycline, oxytetracycline, and gentamycin.

12. The therapeutic device as in claim 1, further comprising a pharmaceutical agent.

13. The therapeutic device as in claim 12, wherein said pharmaceutical agent comprises an antihistamine.

14. The therapeutic device as in claim 12, wherein said pharmaceutical agent is selected from the group consisting of an anticancer agent, an antiviral agent, and an antifungal agent.

15. The therapeutic device as in claim 1, further comprising a biologic.

16. The therapeutic device as in claim 15, wherein said biologic is selected from the group consisting of a hormone and a growth factor.

17. The therapeutic device as in claim 1, further comprising a hemostatic agent.

18. The therapeutic device as in claim 1, further comprising a microorganism.

19. The therapeutic device as in claim 18, wherein said microorganism comprises a vaccine.

20. The therapeutic device as in claim 19, wherein said vaccine comprises a modified live virus.

21. The therapeutic device as in claim 19, wherein said vaccine comprises a killed virus.

22. The therapeutic device as in claim 19, wherein said vaccine comprises vital components.

23. The therapeutic device as in claim 1, further comprising a preservative.

24. The therapeutic device as in claim 23, wherein said preservative is selected from the group consisting of methylparaben and benzethonium chloride.

25. The therapeutic device as in claim 1, further comprising a topical anesthetic.

26. The therapeutic device as in claim 1, further comprising a metal ion.

27. The therapeutic device as in claim 26, wherein said metal ion is selected from the group consisting of zinc, cobalt, iron, and manganese.

28. The therapeutic device as in claim 1, wherein said hydrogel comprises:
about 99% by weight of water, and
about 0.6% by weight of acemannan.

29. The therapeutic device as in claim 1, wherein said therapeutic device is sterilized by radiation.

30. A therapeutic device comprising a dried-hydrogel in the form of a flexible solid foam that can be cut to the shape of a wound or lesion, said therapeutic device having gas bubbles dispersed throughout and being prepared by freeze-drying a hydrogel comprising:
about 98.88% by weight of purified water,
about 0.5% by weight of plasdone,
about 0.002% by weight of benzethonium chloride,
about 0.05% by weight of acemannan, and
about 0.445% by weight of hydroxyethylcellulose, said therapeutic device being capable of being transformed into said hydrogel upon absorption of additional water.

31. The therapeutic device as in claim 30, wherein said therapeutic device is sterilized by radiation.

32. A therapeutic device comprising from about 85% to about 95% by weight of a hydrophilic-hygroscopic therapeutic polysaccharide obtained from aloe vera dispersed in from about 5% to about 15% by weight of liquid medium, said therapeutic device being in the form of a flexible solid foam that can be cut to the shape of a wound or lesion, and said therapeutic device having gas bubbles dispersed throughout and being capable of being transformed into a hydrogel upon absorption of additional liquid medium.

33. The therapeutic device as in claim 32, wherein said liquid medium comprises from about 8% to about 12% by weight of said therapeutic device.

34. The therapeutic device as in claim 32, wherein said liquid medium comprises about 10% by weight of said therapeutic device.

35. The therapeutic device as in claim 32, wherein said hydrophilic-hygroscopic therapeutic polysaccharide obtained from aloe vera comprises acemannan.

36. The therapeutic device as in claim 32, wherein said therapeutic device comprises freeze-dried acemannan hydrogel.

37. The device as in claim 32, wherein said therapeutic device is adhered to an adhesive backing.

38. The therapeutic device as in claim 32, further comprising an antibiotic.

39. The therapeutic device as in claim 38, wherein said antibiotic is selected from the group consisting of tetracycline, oxytetracycline, and gentamycin.

40. The therapeutic device as in claim 32, further comprising a pharmaceutical agent.

41. The therapeutic device as in claim 40, wherein said pharmaceutical agent comprises an antihistamine.

42. The therapeutic device as in claim 40, wherein said pharmaceutical agent is selected from the group consisting of an anticancer agent, an antiviral agent, and an antifungal agent.

43. The therapeutic device as in claim 32, further comprising a biologic.

44. The therapeutic device as in claim 43, wherein said biologic is selected from the group consisting of a hormone and a growth factor.

45. The therapeutic device as in claim 32, further comprising a hemostatic agent.

46. The therapeutic device as in claim 32, further comprising a microorganism.

47. The therapeutic device as in claim 46, wherein said microorganism comprises a vaccine.

48. The therapeutic device as in claim 47, wherein said vaccine comprises a modified live virus.

49. The therapeutic device as in claim 47, wherein said vaccine comprises a killed virus.

50. The therapeutic device as in claim 47, wherein said vaccine comprises vital components.

51. The therapeutic device as in claim 32, further comprising a preservative.

52. The therapeutic device as in claim 51, wherein said preservative is selected from the group consisting of methylparaben and benzethonium chloride.

53. The therapeutic device as in claim 32, further comprising a topical anesthetic.

54. The therapeutic device as in 32, further comprising a metal ion.

55. The therapeutic device as in claim 54, wherein said metal ion is selected from the group consisting of zinc, cobalt, iron, and manganese.

56. The therapeutic device as in claim 32, wherein said therapeutic device is sterilized by radiation.

57. A therapeutic device comprising from about 85% to about 95% by weight of acemannan dispersed in from about 5% to about 15% by weight of water, wherein said therapeutic device being in the form of a flexible solid foam that can be to the shape of a wound or lesion, said therapeutic device having gas bubbles dispersed throughout and being capable of being transformed into a hydrogel upon absorption of additional water.

58. The therapeutic device of claim 57, wherein said therapeutic device is sterilized by radiation.

59. A method of preparing a therapeutic device comprising:
dispersing particles of a hydrophilic-hygroscopic therapeutic polysaccharide obtained from aloe vera in a liquid medium to give a hydrogel; and
removing said liquid medium to give said therapeutic device in the form of a flexible solid foam that can be cut to the shape of a wound or lesion, said therapeutic device having gas bubbles dispersed throughout and being capable of being transformed into said hydrogel upon absorption of additional liquid medium.

60. The method of claim 59, further comprising irradiating said therapeutic device.

61. A method of preparing a therapeutic device comprising:
dispersing particles of a therapeutic polysaccharide obtained from aloe vera in water to give a hydrogel; and
freeze-drying said hydrogel to give said therapeutic device in the form of a flexible solid foam that can be cut to the shape of a wound or lesion, said therapeutic device having gas bubbles dispersed throughout and being capable of being transformed into said hydrogel upon absorption of additional water.

62. The method of claim 61, further comprising irradiating said therapeutic device.

63. A method of treating a wound or lesion in am animal comprising:
applying to said wound or lesion an effective amount of a therapeutic device comprising a dried hydrogel in the form of a flexible solid foam that can be cut to the shape of a wound or lesion, said therapeutic device having gas bubbles dispersed throughout, and being prepared by removing a liquid medium from a hydrogel, said hydrogel comprising particles of a hydrophilic-hygroscopic therapeutic polysaccharide dispersed in said liquid medium, wherein said therapeutic polysaccharide is obtained from aloe vera, said therapeutic device being capable of being transformed into said hydrogel upon absorption of additional liquid medium.

64. A method of treating a wound or lesion in an animal comprising:
applying to said wound or lesion an effective amount of a therapeutic device comprising a freeze-dried acemannan hydrogel in the form of a flexible solid foam that can be cut to the shape of a wound or lesion, said therapeutic device having gas bubbles dispersed throughout and being capable of being transformed into a hydrogel upon absorption of additional water.

65. The method of claim 63, wherein said wound or lesion is in the oral cavity of said animal.

66. The method of claim 64, wherein said wound or lesion is in the oral cavity of said animal.

67. The method of claim 66, wherein said animal is a human and said wound or lesion is aphthous ulcers.

68. The method of claim 66, wherein said animal is a human and said wound or lesion is Herpes labialis.

* * * * *

UNITED STATES PATENT AND TRADEMARK OFFICE
CERTIFICATE OF CORRECTION

PATENT NO. : 5,409,703
DATED : April 25, 1995
INVENTOR(S) : Bill H. McAnalley, et al.

It is certified that error appears in the above-indentified patent and that said Letters Patent is hereby corrected as shown below:

Col. 1, line 46, delete "lyric" and insert —lytic—.
Col. 4, line 23, delete "vital" and insert —viral—.

Col. 6, line 39, delete "vital" and insert -- viral --.

Col. 10, line 15, delete "per,formed" and insert -- performed --.

Col. 10, line 55, delete "CD4" and insert -- CD-4 --.

Col. 11, line 47, delete "vital" and insert -- viral --.

Col. 11, line 52, delete "Cartington" and insert -- Carrington --.

Col. 20, line 19, delete "90" and insert -- $\pi$ --.

Col. 21, line 2, delete "Cartington" and insert -- Carrington --.

Col. 21, line 14, delete "Cartington" and insert -- Carrington --.

Col. 21, line 25, delete "vital" and insert -- viral --.

Col. 26, line 32, delete "The-therapeutic" and insert -- The therapeutic --.

UNITED STATES PATENT AND TRADEMARK OFFICE
CERTIFICATE OF CORRECTION

PATENT NO. : 5,409,703
DATED : April 25, 1995
INVENTOR(S) : Bill H. McAnalley, et al.

It is certified that error appears in the above-indentified patent and that said Letters Patent is hereby corrected as shown below:

Col. 26, line 39, delete "vital" and insert -- viral --.

Col. 27, line 59, delete "vital" and insert -- viral --.

Col. 27, line 67, following "in", insert -- claim --.

Col. 28, line 10, following "be", insert -- cut --.

Col. 28, line 46, delete "am" and insert -- an --.

Signed and Sealed this

Twenty-fifth Day of July, 1995

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,409,703
DATED : April 25, 1995
INVENTOR(S) : Bill H. McAnalley, et al.

It is certified that error appears in the above-indentified patent and that said Letters Patent is hereby corrected as shown below:

TITLE PAGE, ITEM [75]

In the Inventors section, following "Judith St. John, Irving", insert --D. Eric Moore, Richardson; Annita Weidenbach, Roanoke; Kenneth M. Yates, Grand Prairie--.

Signed and Sealed this

Fifteenth Day of August, 1995

Attest:

BRUCE LEHMAN

*Attesting Officer*        *Commissioner of Patents and Trademarks*